(12) United States Patent
German et al.

(10) Patent No.: US 9,753,009 B2
(45) Date of Patent: Sep. 5, 2017

(54) METHODS AND APPARATUS FOR TRAPPING AND SIZE RESOLUTION OF NANOPARTICLES AND NANOBUBBLES

(71) Applicant: Revalesio Corporation, Tacoma, WA (US)

(72) Inventors: Sean R. German, Seattle, WA (US); Tony L. Mega, Seattle, WA (US)

(73) Assignee: REVALESIO CORPORATION, Tacoma, WA (US)

( * ) Notice: Subject to any disclaimer, the term of this patent is extended or adjusted under 35 U.S.C. 154(b) by 0 days.

(21) Appl. No.: 14/885,935

(22) Filed: Oct. 16, 2015

(65) Prior Publication Data

US 2016/0041122 A1    Feb. 11, 2016

Related U.S. Application Data

(63) Continuation-in-part of application No. PCT/US2014/034558, filed on Apr. 17, 2014.

(60) Provisional application No. 61/812,791, filed on Apr. 17, 2013, provisional application No. 62/168,696, filed on May 29, 2015.

(51) Int. Cl.
  *G01N 27/447* (2006.01)
  *B01L 3/00* (2006.01)

(52) U.S. Cl.
  CPC .. *G01N 27/44765* (2013.01); *B01L 3/502761* (2013.01); *G01N 27/44743* (2013.01); *G01N 27/44791* (2013.01); *B01L 3/50273* (2013.01); *B01L 2300/0645* (2013.01); *B01L 2300/0896* (2013.01); *B01L 2400/0418* (2013.01); *B01L 2400/0421* (2013.01)

(58) Field of Classification Search
  CPC ....... G01N 27/44765; G01N 27/44791; G01N 27/44743; B01L 3/502715; B01L 2300/0645; B01L 2400/0421; B01L 2400/0418; B01L 2200/10
  See application file for complete search history.

(56) References Cited

U.S. PATENT DOCUMENTS

| | | |
|---|---|---|
| 2,656,508 A | 10/1953 | Coulter |
| 2003/0052002 A1 | 3/2003 | Vogel et al. |
| 2010/0025263 A1 | 2/2010 | White et al. |
| 2010/0122907 A1 | 5/2010 | Stanford et al. |
| 2012/0222958 A1 | 9/2012 | Pourmand et al. |
| 2012/0261261 A1 | 10/2012 | Huber |
| 2013/0048499 A1 | 2/2013 | Mayer et al. |

OTHER PUBLICATIONS

"Frequently Asked Questions," National Nanotechnology Initiative website, accessed via the internet on May 30, 2012 at <http://www.nano.gov/nanotech-101/nanotechnology-facts>.

Behrens et al., "The charge of glass and silica surfaces." The Journal of Chemical Physics, vol. 115, No. 14, 2001, 6716-6721.

(Continued)

*Primary Examiner* — J. Christopher Ball
(74) *Attorney, Agent, or Firm* — Knobbe, Martens, Olson & Bear, LLP

(57) ABSTRACT

Provided are systems and methods for accurate size determination of nanoparticles and nanobubbles, comprising detecting multiple repeated translocations of a captured nanoparticle or nanobubble across the sensing zone of a conical nanopore in fluid communication with a fluid comprising nanoparticles or nanobubbles.

37 Claims, 21 Drawing Sheets

(56) References Cited

OTHER PUBLICATIONS

Berge et al., "A novel method to study single-particle dynamics by the resistive pulse technique," Review of Scientific Instruments, 60(8), 1989, pp. 2756-2763.
Berge et al., "Off-axis response for particles passing through long apertures in Coulter-type counters," Measurement Science and Technology, 1(6), 1990.
Berge, "Dissolution of air bubbles by the resistive pulse and the pressure reversal technique," Journal of Colloid and Interface Science, 134(2), Feb. 1990, pp. 548-562.
Boyd et al., "Precision of size determination of resistive electronic particle counters," Journal of Plankton Research, 17(1), 1995, pp. 41-58.
Browning et al., "Current Opinion in Solid State and Matericals Science," Current Opinion in Solid State & Materials Science, 16, 2012, pp. 23-30.
Deblois et al, "Counting and Sizing of Submicron Particles by the Resistive Pulse Technique," Review of Scientific Instruments, 41(7), Jul. 1970, pp. 909-916.
Deblois et al., "Electrokinetic measurements with submicron particles and pores by the resistive pulse technique," Journal of Colloid and Interface Science, vol. 61, Issue 2, Sep. 1977, pp. 323-335.
Domingos et al., "Characterizing Manufactured Nanoparticles in the Environment: Multimethod Determination of Particle Sizes," Environmental Science and Technology, 43(19), 2009, 7277-7284.
Filipe et al., "Critical Evaluation of Nanoparticle Tracking Analysis (NTA) by NanoSight for the Measurement of Nanoparticles and Protein Aggregates," Pharmaceutical Research, vol. 27, Issue 5, May 2010, pp. 796-810.
Firnkes et al., "Electrically Facilitated Translocations of Proteins through Silicon Nitride Nanopores: Conjoint and Competitive Action of Diffusion, Electrophoresis, and Electroosmosis," Nano Letters, 10(6), Jun. 2010, pp. 2162-2167.
Fologea et al., "Slowing DNA Translocation in a Solid State Nanopore," Nano Letters, 5(9), Sep. 2005, pp. 1734-1737.
Gao et al., "A simple method of creating a nanopore-terminated probe for single-molecule enantiomer discrimination," Analytical Chemistry, 81(1), Jan. 1, 2009, pp. 80-86.
German et al., "Controlling Nanoparticle Dynamics in Conical Nanopores," Journal of Physical Chemistry C, 117(1), 2013, pp. 703-711.
Gershow et al., "Recapturing and Trapping Single Molecules with a Solid States Nanopore," National Nanotechnology, 2(12), Dec. 2007, pp. 775-779.
Golibersuch, "Observation of Aspherical Particle Rotation in Poiseuille Flow via the Resistance Pulse Technique," Biophysics Journal, 13(3) Mar. 1973, pp. 265-280.
Hurley, "Sizing Particles with a Coulter Counter," Biophysics Journal, 10(1), Jan. 1970, pp. 74-79.
Ito et al., "Simultaneous Determination of the Size and SUrface Charge of Individual Nanoparticles Using a Carbon Nanotube-Based Coulter Counter," Analytical Chemistry, 75(10), May 15, 2003, pp. 2399-2406.
Kozak et al., "Advances in Resistive Pulse Sensors: Devices bridging the void between molecular and microscopic detection," Nano Today, 6(5), Oct. 2011, pp. 531-545.
Kozak et al., "Simultaneous Size and z-Potential Measurements of Individual Nanoparticles in Dispersion using Size-Tunable Pore Sensors," ACS Nano, 6(8), 2012, pp. 6990-6997.
Lan et al., "Diffusional Motion of a Particle Translocation through a Nanopore," ACS Nano, 6(2), 2012, pp. 1757-1765.
Lan et al., "Nanoparticle Transport in Conical-Shaped Nanopores," Analytical Chemistry, vol. 83, No. 10, 2011, pp. 3840-3847.
Lan et al., "Pressure-Dependent Ion Current Rectification in Conical-Shaped Glass Nanopores," Journal of the American Chemical Society, 133(34), 2011, pp. 13300-13303.
Lan et al., "Pressure-Driven Nanoparticle Transport across Glass Membranes Containing a Conical-Shaped Nanopore," The Journal of Physical Chemistry C, 115(38), 2011, pp. 18445-18452.
Lan, "Particle Transport and Ion Current Rectification in Conical-Shaped Nanopores," Doctoral Dissertation, The University of Utah, 2011, 171 pages.
Li et al., "Fabrication of Glass Nanopore Electrodes for Single-molecule Detection of β-Cyclodextrin," Chinese Journal of Analytical Chemistry, vol. 38, Issue 12, Dec. 2010, pp. 1698-1702.
Luo et al., "Resistive-Pulse Analysis of Nanoparticles," Annual Review of Analytical Chemistry, 7, Jun. 2014, pp. 513-535.
Madani et al., "Measurement of Polydisperse Colloidal Suspensions with quasielastic light scattering," Particle & Particle Systems Characterization, 8(1-4), 1991, pp. 259-266.
Murray et al., "Nanoelectrochemistry: Metal Nanoparticles, Nanoelectrodes, and Nanopores," Chemical Reviews, 108(7), Jun. 18, 2008, pp. 2688-2720.
Qin et al., "Effects of particle's off-axis, shape, orientation and entry position on resistance changes of micro Coulter counting devices," Measurement Science and Technology, 22(4), Apr. 2011.
Rasteiro et al., "Nanoparticle Characterization by PCS: The Analysis of Bimodal Distributions," Particulate Science and Technology: An International Journal, 26(5), 2008, pp. 413-457.
Ruf, "Treatment of Contributions of Dust to Dynamic Light Scattering Data," Langmuir, 18(10), 2002, pp. 3804-3814.
Schiel et al., "Diffusion and Trapping of Single Particles in Pores with Combined Pressure and Dynamic Voltage," Journal of Physical Chemistry C, 118(33), 2014, pp. 19214-19223.
Schoch et al., "Transport phenomena in ananofluidics," Reviews of Modern Physics, 80(3), Jul. 2008, pp. 839-883.
Sen et al., "Enhanced discrimination of DNA molecules in nanofluidic channels through multiple measurements," Lab on a Chip, 12(6), 2012, pp. 1094-1101.
Stöckle et al., "High-quality near-field optical probes by tube etching," Applied Physics Letters, vol. 75, No. 2, Jul. 12, 1999, pp. 160-162.
Takamura et al., "Low-voltage electoosmosis pump for stand-alone micofluidics devices," Electrophoresis, 24(1-2), 2003, pp. 185-192.
Vercoutere et al., "Rapid discrimination among individual DNA hairpin molecules at single-nucleotide resolution using an ion channel," Nature Biotechnology, 19, 2001, pp. 248-252.
Vogel et al., "A Variable Pressure Method for Characterizing Nanoparticle Surface Charge Using Pore Sensors," Analytical Chemistry, 84(7), 2012, pp. 3125-3131.
Wanunu et al., "DNA Translocation Goverend by Interactions with Solid-State Nanopores," Biophysical Journal, vol. 95, Issue 10, Nov. 15, 2008, pp. 4716-4725.
White et al., "Ion Current Rectification at Nanopores in Glass Membranes," Langmuir, 24(5), 2008, pp. 2212-2218.
Wu et al., "Protein Nanopores with Covalently Attached Molecular Adapters," Journal of the American Chemical Society, 129(51), Nov. 30, 2007, pp. 16142-16148.
Zhang et al., "A Silica Nanochannel and Its Applications in Sensing and Molecular Transport," Analytical Chemistry, 81(13), 2009, pp. 5541-5548.
International Search Report mailed Aug. 27, 2014, in International Patent Application No. PCT/US2014/034558, filed Apr. 17, 2014.

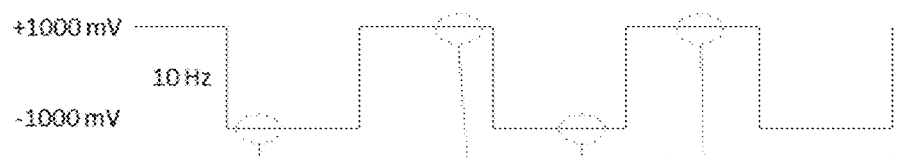
FIG. 5A
FIG. 5B
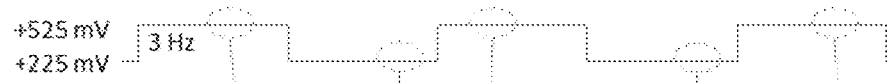
FIG. 5C
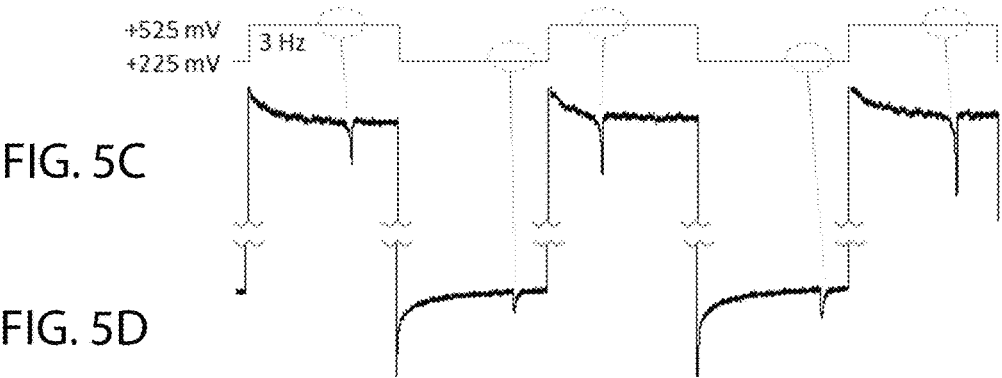
FIG. 5D

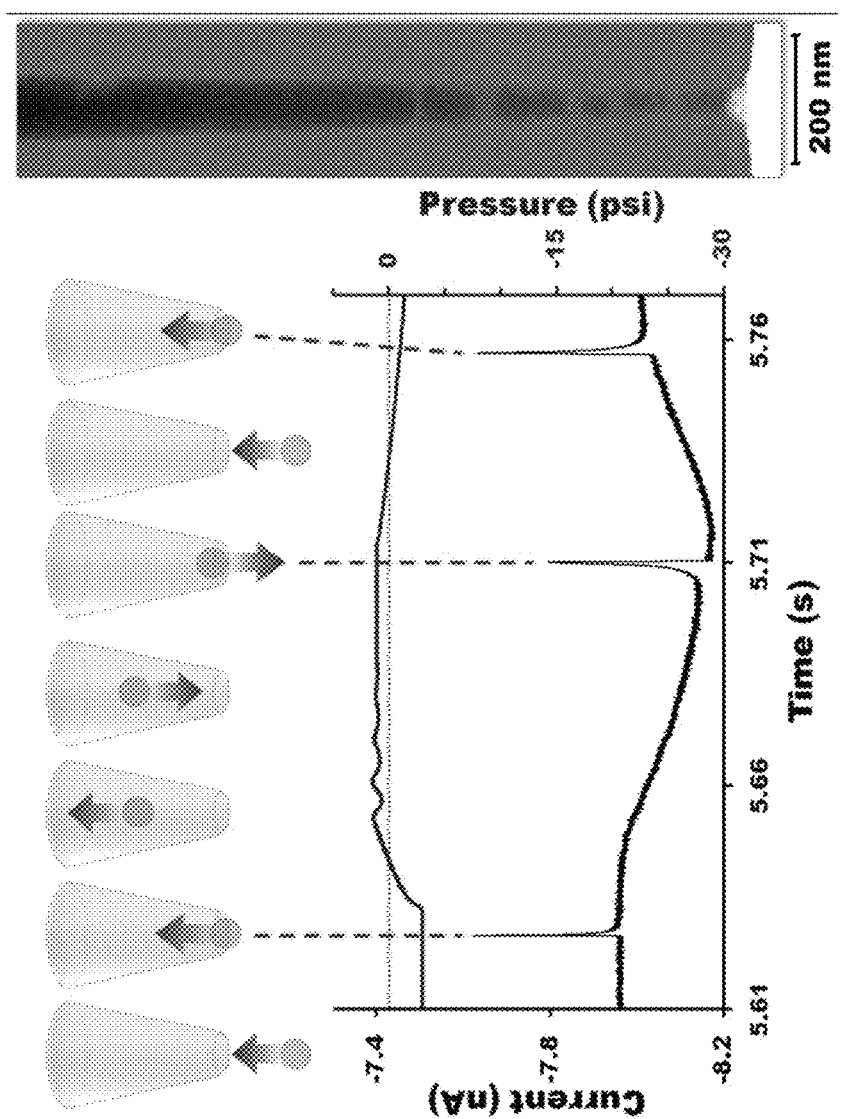

FIG. 14A
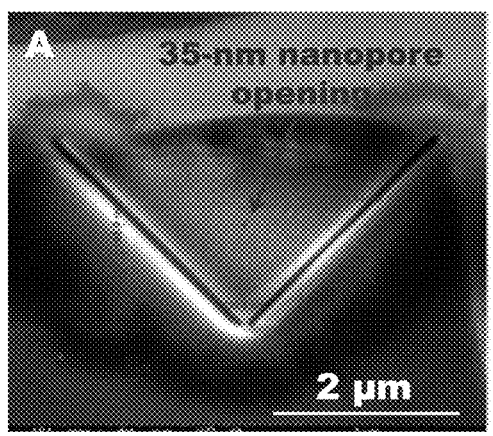
FIG. 14B
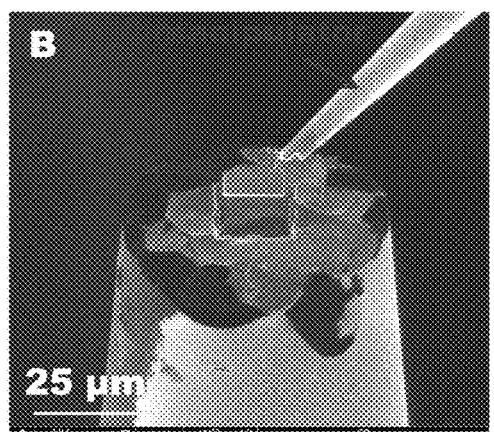
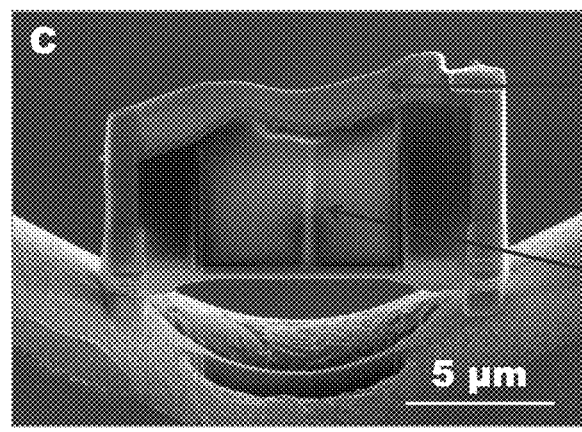
FIG. 14C

METHODS AND APPARATUS FOR TRAPPING AND SIZE RESOLUTION OF NANOPARTICLES AND NANOBUBBLES

CROSS-REFERENCE TO RELATED APPLICATIONS

This application is a continuation-in-part of PCT/US2014/034558, filed Apr. 17, 2014, which claims the benefit of U.S. Provisional Patent Application No. 61/812,791, filed Apr. 17, 2013. This application also claims the benefit of U.S. Provisional Patent Application No. 62/168,696, filed May 29, 2015. The contents of which are incorporated herein by reference in their entirety.

FIELD OF THE INVENTION

Preferred aspects of the invention relate to accurate size determination of nanoparticles and nanobubbles comprising detecting multiple repeated translocations of a captured nanoparticle or nanobubble across the sensing zone of a conical nanopore.

Additional aspects of the invention generally relate to systems and methods for manipulating and characterizing nanobubbles and nanoparticles in solution, and more particularly related to systems and methods comprising use of conical-shaped nanopores (e.g., glass, or other suitable material) having a sensing zone with a half-cone angle sufficiently small to provide for significant channel-like character at the nanopore, wherein adjusting at least one parameter selected from electrophoretic force (EPF), electroosmotic force (EOF), and pressure across the nanopore, provides for fine control of nanoparticle or nanobubble translocation velocities across the sensing zone of the nanopore (e.g., by shifting the zero velocity point to an applied voltage/potential to provide for an acceptable signal-to-noise ratio) to provide methods detecting, manipulating and characterizing nanobubbles and nanoparticles in solution.

BACKGROUND OF THE INVENTION

Characterization of the size, geometry, charge, and dynamic properties of individual nanoscale objects in bulk solution presents a significant challenge, particularly for objects at the lower end of the scale, yet a high-resolution method for characterization of nanoparticle size in bulk solution is lacking. The present work relates to a means of measuring particle size in solution with a resolution below 1 nanometer.

Currently, dynamic light scattering (DLS), electron microscopy (EM), and nanoparticle tracking analysis (NTA) are the most commonly used techniques for nanoparticle characterization, although these techniques are prone to artifacts (Domingos, R., et al., Environ. Sci. Technol 43:7277, 2009). Furthermore, the basis for each limits their usefulness. For example, DLS is an ensemble measurement commonly used to measure particle size and charge in bulk solution and is well suited for monodisperse systems, but its ability to resolve peaks of multi-modal distributions is controversial (Rasteiro, M., et al., Particul Sci Technol 2008, 26, 413-437; Ruf, H. Langmuir 2002, 18, 3804-3814; Madani, H., et al., Part Part Syst Char 1991, 8, 259-266), and a resolution of particle size ratios below 3:1 is often questioned. Furthermore, DLS accuracy suffers increasingly with reductions in particle concentration and/or size (particularly below ~20 nm) (Domingos, R., et al., Environ. Sci. Technol 2009, 43, 7277). EM provides an exceptional size resolution of ~0.2 nm for particles removed from solution and placed under vacuum but has yet to be used routinely for particles in solution (DeBlois, R. W., et al., Rev Sci Instrum 1970, 41, 909-916.). NTA has recently gained popularity and is based on tracking the 2D diffusion rate of individual particles spending a sufficient length of time in the plane of observation. Under ideal conditions, DLS and NTA both can be accurate to 2%, but more difficult samples can have errors an order of magnitude larger (Gao, C., et al., Anal. Chem 2009, 81, 80-86).

By contrast, nanopores provide a method that measures individual nanoscale particles in bulk solution as well as providing information about particle charge. Recent adaptations of the Coulter-counter technique to the nanoscale range have been used as a label-free method for studying biological molecules, especially DNA, and nanoparticles having a variety of compositions and surface charges (DeBlois, R. W., et al., Journal of Colloid and Interface Science 61:323-335, 1977). In these techniques, an electrical potential difference is applied between the electrodes on the two sides of a nanopore. Nanoparticles passing through the pore cause a brief decrease in the electrical current plotted as a function of time. The duration, magnitude, and shape of these current-time profiles provide a wealth of information about the variety of forces that act on the nanoparticles as they pass through the pore (Domingos, R., et al., Environ. Sci. Technol 43:7277, 2009; and Lan, W.-J., et al., Anal. Chem 83:3840-3847, 2011). However, large particle velocities can limit/exclude the application of nanopore techniques to a significant portion of the nanoscale range.

Reliable detection and characterization of small nanoparticles is limited by Electronic filtering, which for typical bandwidths of 10 kHz leads to underestimation of peak heights for detectable particles and can even entirely miss particles below 40 nm for certain pore geometries (Lan, W.-J., et al., Anal. Chem 83:3840-3847, 2011). Innovative attempts to overcome the problem of excessive translocation speed include chemical modification of pores (Wu, H.-C., et al., J. Am. Chem. Soc 129:16142-16148, 2007) and variations in pore size (Wanunu, M., et al., Biophysical Journal 95:4716-4725, 2008), shape (Wanunu, M., et al., Nature Nanotech 5:807-814, 2010), salt concentration, temperature, and solution viscosity (Fologea, D., et al., Nano Letters 5:1734-1737, 2005), as well as employing repeated measurements of individual particles (Berge, L. I., et al., Review of Scientific Instruments 60:2756, 1989; and Gershow & Golovchenko, Nature Nanotech 2:775-779, 2007). By varying pH to adjust the difference in zeta potential between the particle and the pore, Firnkes et al. were able to manipulate the effective velocity of a single protein and reverse the translocation driving force from electrophoretic to electroosmotic (Firnkes, M., et al., Nano Letters 10:2162-2167, 2010). While this method provides an important step forward in controlling particle speed, significant diffusion rates across the 10-nm wide pore yet reduce signal fidelity.

Cylindrical carbon nanotubes (Lan, W.-J., et al., Anal. Chem 83:3840-3847, 2011) and glass nanochannels (Ito, T., et al., Anal. Chem 75:2399-2406, 2003) have been used to characterize 60-nm and 40-nm particles, respectively, but measurement of smaller particles was hindered by low signal-to-noise ratios. By contrast, focusing of the sensing zone in conical nanopores to a much smaller volume imparts many advantages including high signal-to-noise ratios and asymmetric peak shapes, which provide information about translocation direction (Wu, H.-C., et al., J. Am. Chem. Soc 129:16142-16148, 2007). Recently, Vogel et al. reported a method for characterizing the surface charge of 200-nm particles based upon resistive pulse sensing in conical nanopores under variable pressure (Vogel, R., et al., *Anal. Chem* 84:3125-3131, 2012). The elastomeric pores used in these studies have the advantage that they can be dynamically varied in size; however, the hydrophobic nature of this pore material may lead to undesirable interactions with hydrophobic analytes and solvents other than water. By contrast, the hydrophilic surfaces of silicon nitride (SiN) and glass nanopores (GNPs) are often desirable for studies involving both hydrophobic and hydrophilic analytes. SiN-based nanopores are frequently used since they have the advantage that one can readily measure their pore size during manufacturing. Despite this advantage, SiN chip type pores have limited usefulness for nanoparticles below 40 nm due to noise problems, and their manufacturing process is complex and expensive.

By contrast, simple and inexpensive methods exist for producing GNPs that can detect molecules as small as 1.5 nm (Gao, C., et al., *Anal. Chem* 81:80-86, 2009; and Li, G.-X., et al., *Chinese Journal of Analytical Chemistry* 38:1698-1702, 2010). In addition to hydrophilicity, GNPs have numerous advantages compared to other types of pores in terms of exceptional electrical properties for high bandwidth measurements, ability to withstand high pressure, compatibility with optical measurements, chemical stability, and the possibility to modify their surface with a variety of functional groups. Gao et al. reduced particle velocities sufficiently to detect 10-nm gold nanoparticles by producing GNPs near the threshold at which the particle could pass through (Gao, C., et al., *Anal. Chem* 81:80-86, 2009). Though inadequate for general control of particle dynamics, this approach did provide a method for determining pore size, which was not possible using electron microscopy (Gao, C., et al., *Anal. Chem* 81:80-86, 2009; and Li, G.-X., et al., *Chinese Journal of Analytical Chemistry* 38:1698-1702, 2010).

Nanobubbles.

There is no information or suggestion in the art as to whether nanopores (e.g., GNPs) would have any utility for characterization of the geometry, charge, and dynamic properties of nanobubbles of any size.

SUMMARY OF THE INVENTION

Aspects of the present invention relate to controlling the forces acting on a nanoparticle or nanobubble as it passes through a nanopore.

In certain aspects, the velocity of a nanoparticle (e.g., Au nanoparticle) or nanobubble can be controlled over 3 orders of magnitude by balancing the pressure, electrophoretic and electroosmotic forces acting on it.

According to particular aspects, the nanoparticle or nanobubble velocity can be controlled with high precision by adjusting the voltage across the nanopore, allowing observation of nanoparticle or nanobubble translocation that would normally be too rapid to be observed by applying either an electrical or pressure force alone.

According to additional aspects, cancellation of the electrical and pressure forces allows observation of the random motion of a nanoparticle or nanobubble as it moves through the nanopore.

According to further aspects, these fundamental results are unprecedented, and have substantial utility in applications for studying particle or nanobubble dynamics, and in the analysis of nanoparticles and nanobubbles, and the conclusions provide for a wide range of applications for characterization of nanoparticles, nanobubbles and macromolecules.

According to particular aspects, the threshold condition is further investigated, with demonstrated control of velocities over three orders of magnitude for exemplary nanoparticles (e.g., 8-nm nanoparticles) or nanobubbles in glass nanopores (GNPs).

Additional aspects provide a rationale for controlling nanoparticle or nanobubbles dynamics by balancing the pressure, electrophoretic (EPF), and electroosmotic (EOF) forces (FIG. 1), wherein this balance of three forces provides for previously unattainable control over particle dynamics in a conical pore.

In particular aspects, fine control of particle velocities is provided by taking advantage of electroosmosis and by applying a constant pressure to shift the zero velocity point to a potential with acceptable signal-to-noise ratio.

Further aspects provide finite element analysis (FEA) simulations that model the experimental results.

Additional aspects provide insights into pore geometry, spatial distribution of nanoparticle and nanobubble velocities within the pore, and the influence of both the nanoparticle or nanobubble surface, and the pore surface charge densities.

Certain aspects provide systems and methods for detecting, manipulating and characterizing nanobubbles and nanoparticles in solution, comprising: providing a saline solution having nanoparticles or nanobubbles; providing a conical-shaped nanopore having a nanopore diameter, a proximal end, a distal end in communication with the saline solution, and having a nanoparticle or nanobubble sensing zone between the proximal and the distal ends, and wherein the sensing zone of the conical-shaped nanopore has a half-cone angle sufficiently small to provide for significant channel-like character at the nanopore; applying, using an electrode, a voltage/potential across the nanopore to provide an electrophoretic force (EPF) across the nanopore; subjecting the nanopore to an electroosmotic force (EOF); applying a pressure across the nanopore; and adjusting at least one parameter selected from EPF, EOF, and pressure across the nanopore, to provide for fine control of particle or nanobubble translocation velocities across the sensing zone of the nanopore (e.g., by shifting the zero velocity point to an applied voltage/potential to provide for an acceptable signal-to-noise ratio), to provide a method for detecting, manipulating and characterizing nanobubbles and nanoparticles in solution.

Preferred aspects provide a method for determining the size and/or shape of nanobubbles and nanoparticles in solution, comprising: placing a conical-shaped nanopore in fluid communication with a fluid having nanoparticles or nanobubbles, the conical nanopore having a half-cone angle, a nanopore diameter, a proximal end, a distal end in communication with the fluid, and a nanoparticle or nanobubble sensing zone between the proximal and the distal ends; capturing a nanoparticle or nanobubble from the fluid into the nanopore; translocating the captured nanoparticle or nanobubble across the sensing zone toward the proximal end by applying a differential pressure across the sensing zone, and/or by applying a voltage across the sensing zone, to provide a proximal translocation of the captured nanoparticle or nanobubble, and detecting a resistive pulse caused by the proximal translocation; triggering, upon detection of the resistive pulse caused by the proximal translocation, a reversal of the direction of the differential pressure, and/or a reversal of the voltage across the sensing zone, and translocating the captured nanoparticle or nanobubble across the sensing zone toward the distal end to provide a distal translocation of the captured nanoparticle or nanobubble, and detecting a resistive pulse caused by the distal translocation; triggering, upon detection of the resistive pulse caused by the distal translocation, a reversal of the direction of the differential pressure, and/or a reversal of the voltage across the sensing zone, and translocating the captured nanoparticle or nanobubble across the sensing zone toward the proximal end to provide an additional proximal translocation of the captured nanoparticle or nanobubble; repeating the preceding triggering to provide for multiple proximal and distal translocations of the captured nanoparticle or nanobubble across the sensing zone and detecting multiple respective resistive pulses; and determining a size and/or shape of the captured nanoparticle or nanobubble based on properties of the detected multiple resistive pulses.

In certain aspects translocating is by applying a differential pressure across the sensing zone (e.g., by applying the differential pressure across the sensing zone comprising use of a differential pressure regulator capable of controlling the pressure inside the nanopore relative to an external pressure, and wherein the pressure inside the nanopore can be positive or negative relative to the external pressure). In certain aspects translocating is by applying a voltage across the sensing zone using electrodes (e.g., by applying a voltage across the sensing zone comprising use of electrodes positioned on opposite sides of the conical-shaped nanopore, the electrodes in communication with a voltage/potential source, and configured to provide for application of a voltage/potential across the sensing zone). In certain aspects the fluid is an aqueous saline solution.

In certain aspects, the sensing zone of the conical-shaped nanopore has a half-cone angle sufficiently small to provide for significant channel-like character at the nanopore. In certain aspects, determining the size and/or shape of the captured nanoparticle or nanobubble based on properties of the detected multiple resistive pulses comprises analyzing current-time traces of the multiple resistive pulses (e.g., comprising exporting and analyzing the current time-traces using suitable computer-implemented data acquisition hardware and software). The computer-implemented data acquisition hardware and software may comprise a data acquisition (DAQ) card. The computer-implemented data acquisition hardware and software may comprise a field-programmable gate array (FPGA) card.

The nanoparticles or nanobubbles may have a diameter in a range selected from the size range group consisting of 8 nM to 10 nM, 8 nM to 20 nM, 8 nM to 30 nM, 8 nM to 40 nM, 8 nM to 50 nM, 8 nM to 100 nM and 100 nm to 1 micron.

In certain aspects, proximal and distal translocations of the particle or the nanobubble are repeated for a number of times selected from the group consisting of at least 2, at least 5, at least 10, at least 15, at least 20, at least 25, at least 30, at least 40, at least 50, at least 60, at least 70, at least 80, at least 90 and at least 100 times. In certain aspects, proximal and distal translocations of the particle or the nanobubble are repeated multiple times within a time period selected from the group consisting of 20 milliseconds, 40 milliseconds, 100 milliseconds, 0.5 second, 1 second, 5 seconds, 10 seconds, 30 seconds and 1 min (e.g., repeated multiple times, with each cycle (repeat frequency) being about 20 milliseconds; or multiple times within a time period of about 30 seconds).

In certain aspects, determining the size and/or shape (e.g., spherical, asphericity, oblate or prolate) of the captured nanoparticle or nanobubble based on properties of the detected multiple resistive pulses comprises determining the radius of the nanoparticle or nanobubble.

In certain aspects, the differential/applied pressure, in one direction or another (+ or −), is between 0.2 and 10 psi, between −5 psi and 5 psi, or between about −1 psi and 3 psi. In certain aspects, the half-cone angle of the conical nanopore has a value in the range of 0.1 degrees to 4 degrees (e.g., about 2 degrees; 0.2 degrees to 4 degrees; 0.3 degrees to 4 degrees; 0.4 degrees to 4 degrees), to provide for achieving a suitable balance of the forces controlling dynamics of the nanoparticle or nanobubble. In certain aspects, the nanoparticles or nanobubbles have a diameter of less than 8 nM, less than 10 nM, less than 20 nM, less than 30 nM, less than 40 nM, less than 50 nM, or less than 100 nm. In certain aspects, the applied voltage/potential, in one direction or another (+ or −), is between 100 and 500 mV, −100 mV and 900 mV, between −250 mV and 900 mV, or about 250 mV. In certain aspects using saline fluid, the salt concentration is between 100 mM and 1 M, 300 mM and 1 M, 500 mM and 1 M, about 150 mM, about 300 mM, or from 150 mM to about 300 mM sodium chloride. In certain aspects, the nanobubbles are oxygen nanobubbles e.g., RNS60 as known in the art).

Yet additional aspects provide a system or device for determining the size and/or shape of nanobubbles and nanoparticles in solution, comprising: a conduit, for a fluid having nanoparticles or nanobubbles, configured to be placed in communication with a source of the fluid; a conical-shaped nanopore (e.g., conical-shaped glass nanopore) having a half-cone angle, a nanopore diameter, a proximal end, a distal end in communication with the fluid conduit, the conical-shaped nanopore having a nanoparticle or nanobubble sensing zone between the proximal and the distal ends, and wherein the sensing zone of the conical-shaped nanopore has a half-cone angle sufficiently small to provide for significant channel-like character at the nanopore; a chamber containing the saline solution and the nanopore, wherein the chamber is in communication with a source of pressure; electrodes (e.g., an electrode pair) positioned on opposite sides of the conical-shaped nanopore, the electrodes in communication with a voltage/potential source, and configured to provide for application of a voltage/potential across the nanoparticle or nanobubble sensing zone between the proximal and the distal ends to provide an electrophoretic force (EPF) across the nanopore; a nanopore/electrode holder in communication with a differential pressure regulator capable of maintaining the pressure inside the conical-shaped nanopore at a constant pressure which can be positive or negative relative to the pressure of the chamber; a current measuring component (e.g., a suitable amplifier) configured to be in operative communication with computer-implemented data acquisition software suitable to analyze and export current-time traces; and control means for adjusting at least one parameter selected from voltage across and pressure inside the nanopore, to provide for fine control of particle or nanobubble translocation velocities across the sensing zone of the nanopore, to provide a method for detecting, manipulating and characterizing nanobubbles and nanoparticles in solution.

The system may further comprise suitable computer-implemented data acquisition hardware and software for exporting and analyzing current-time traces of multiple resistive pulses (e.g., comprising a data acquisition (DAQ) card and/or a field-programmable gate array (FPGA) card). In certain aspects, the software is suitable to determine translocation peak parameters such as peak position, height, and width at half-height as a function of applied voltage.

BRIEF DESCRIPTION OF THE DRAWINGS

FIGS. 5A, 5B, 5C, and 5D show, according to particular exemplary aspects, i-t traces showing a single nanoparticle repeatedly going in and out of a nanopore as the applied potential is reversed.

FIGS. 13A, 13B, and 13C show, according to particular exemplary aspects, (A) illustration of nanoparticle motion during particle reversal experiments. (B) Crosssectional image of a glass nanopore obtained by FIB/SEM. The image is of a section parallel to the pore axis including the pore opening where salt has accumulated during the drying process. (C) Plot of current (black trace) and differential pressure (blue trace) vs time, showing three translocations of a nominally 59-nm-radius particle. The initial current value at 5.61 s represents an open pore held constant at −300 mV applied potential. When −3 psi is applied (corresponding to a lower pressure within the capillary relative to the external solution), the solution is pulled into the capillary, resulting in a particle passing through the pore sensing zone at 5.63 s. The translocation pulse triggers a reversal of the pressure to 1 psi which is sufficient to force the same particle back out of the pore at 5.71 s, triggering a second reversal of pressure. This process of passing the particle back and forth through the pore can be continued indefinitely until the particle is lost by diffusion or the experiment terminated. The approximate mirror symmetry in the shapes of alternating resisitve pulses reflects a particle entering and exiting the conical-shaped pore. The current baseline falls and rises with the pressure swings as described in the text.

FIGS. 14A, 14B, and 14C show, according to particular exemplary aspects, details regarding the preparation of nanopore lamella for TEM. (A) Image of a 35-nm nanopore opening and markers to reference the nanopore position after it is covered with a protective layer of platinum. (B) In situ "lift out" of a lamella containing the nanopore attached to an OmniProbe nanomanipulator. (C) The polished lamella attached to a TEM holder. An FEI DB235 Dual-Beam Focus Ion Beam System was used for this work. Prior to FIB/SEM, the glass nanopore was plasma cleaned and coated with 2 nm of gold to minimize charging. The pore opening was found directly in the middle of the 60-µm diameter glass face. Two perpendicular lines were milled as fiducial markers for the pore location just prior to depositing a 700 nm thick layer of platinum as a protective layer over the top of the pore opening. Parallel trenches on opposite sides of the nanopore were milled to allow extraction of the lamella with the OmniProbe. The lamella was transferred to a TEM holder and further thinned and polished to a final thickness of 300 nm for imaging using STEM.

FIG. 15A shows an automated pressure-based trapping and particle sizing system. The glass nanopore and solution containing the particles (1) are placed inside a pressurized custom-built chamber. A pressure regulator controlling the chamber pressure is referenced to a dual proportional valve differential pressure regulator; the latter rapidly increases or decreases the pressure inside the capillary-based nanopore relative to the outer chamber. A patch clamp amplifier operating in voltage clamp mode reports the i-t trace from the nanopore via an AD/DA converter to a custom Labview program that sends control signals to the pressure regulators upon detection of a resistive pulse. The differential pressure control is accurate to within 0.08 mmHg Both the i-t trace and the differential pressure readout are recorded by the patch clamp amplifier to ensure synchronized timing, thereby, allowing the correlation of pressure and pulse duration. The cycle of events for moving the nanoparticle back and forth across the nanopore orifice are: (1) a particle translocation event occurs; (2) the resulting resistive pulse is amplified and the i-t trace is passed to a DAQ card; (3) a LabVIEW program monitors the slope of the trace to detect the event; (4) a signal to the electronic regulator reverses the sign of the differential pressure; and (5) after a delay of ~20 ms, the direction of fluid flow is reversed, forcing the particle in the opposite direction back through the sensing zone. This process is repeated until sufficient measurement cycles are obtained to determine the particle size, or until the particle is lost by diffusion. In the experiments reported here, typically 20 to 70 cycles were repeated to determine particle size. FIG. 15B shows an automated voltage-based trapping and particle sizing system. The glass nanopore and solution containing the particles (1) are contained in a pressurized custom-built chamber. A pressure regulator controlling the chamber pressure is referenced to a dual proportional valve differential pressure regulator; the latter can hold constant the pressure inside capillary-based nanopore either positive or negative relative to the outer chamber. The cycle of events for moving the nanoparticle back and forth across the nanopore orifice are: (1) a particle translocation event occurs; (2) the resulting resistive pulse is amplified, and the i-t trace is passed to an FPGA card; (3) the FPGA card monitors the slope of the trace to detect the event; (4) a signal to the amplifier changes the voltage applied within the nanopore, thereby changing the electrokinetics to recapture the particle back through the sensing zone. This process is repeated until sufficient measurement cycles are obtained to determine the particle size, or until the particle is lost by diffusion.

DETAILED DESCRIPTION OF THE INVENTION

Conical nanopores are a powerful tool for characterizing nano-scale particles and even small molecules. Although the technique provides a wealth of information, such pores are limited in their ability to investigate particle dynamics below ~40 nm due to high particle velocities through a very short sensing zone, and nothing is known or suggested in the art about whether conical nanopores would be efficacious characterizing nanobubbles (e.g., air, oxygen or other gas(es) nanobubbles).

Particular aspects provide methods for detecting, manipulating and characterizing nanobubbles and nanoparticles in solution, comprising balancing electrokinetic forces acting on nanoparticles (e.g., 8 nm or in the range of, for example 3 to 40 nm diameter) by application of pressure to provide for sufficient slowing of the particle velocity to enable detection and characterization.

According to additional aspects, nanoparticles having different zeta potentials were studied in conical nanopores by varying salt concentration, applied pressure, and potential to reveal the point at which forces are balanced and the particles reverse direction through the nanopore, and adjusting these conditions allows the characterization of nano particles and their dynamics down to the smallest end of the nanoscale range.

According to preferred aspects, the methods are applicable for detecting, manipulating and characterizing nanobubbles in solution.

According to particular aspects, the velocity of 8-nm nanoparticles (e.g., 8 nm, or in the range of X to Y nm) can be controlled in glass conical nanopores by applying pressure and varying voltage to balance electrophoretic (EPF) and electroosmotic (EOF) forces.

Figure 1:
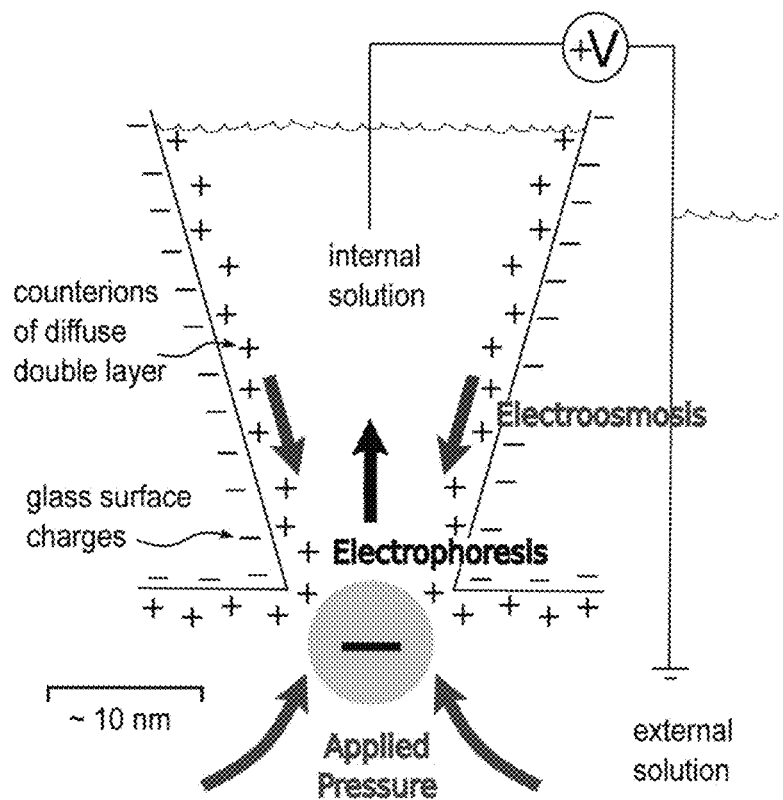
FIG. 1 is a diagram showing, according to particular exemplary aspects of the present invention, driving forces that, on balance, determine the velocity of nanoparticle translocation through an exemplary glass conical nanopore.

FIG. 1 is a diagram showing, according to particular exemplary aspects of the present invention, driving forces that on balance determine the velocity of particle (or nanobubble) translocation through an exemplary conical nanopore. For example, during translocation experiments, as described herein, positive potentials applied to an electrode within the pipette and negative pressures applied within the pipette both tend to draw negatively charged particles inward from the external solution. The applied potential also induces a counteracting electroosmotic force that tends to drive particles out of the pipette into the external solution. The balance of these different forces determines the velocity of particle translocations. This fine control allows characterization of particles in a previously unattainable size range, and is also applicable to nanobubbles, including very small nanobubbles (e.g., less than 100 nm, less than 50 nm, less than 10 nm, less than 5 nm, and less than 2 nm in diameter).

Figure 15A:
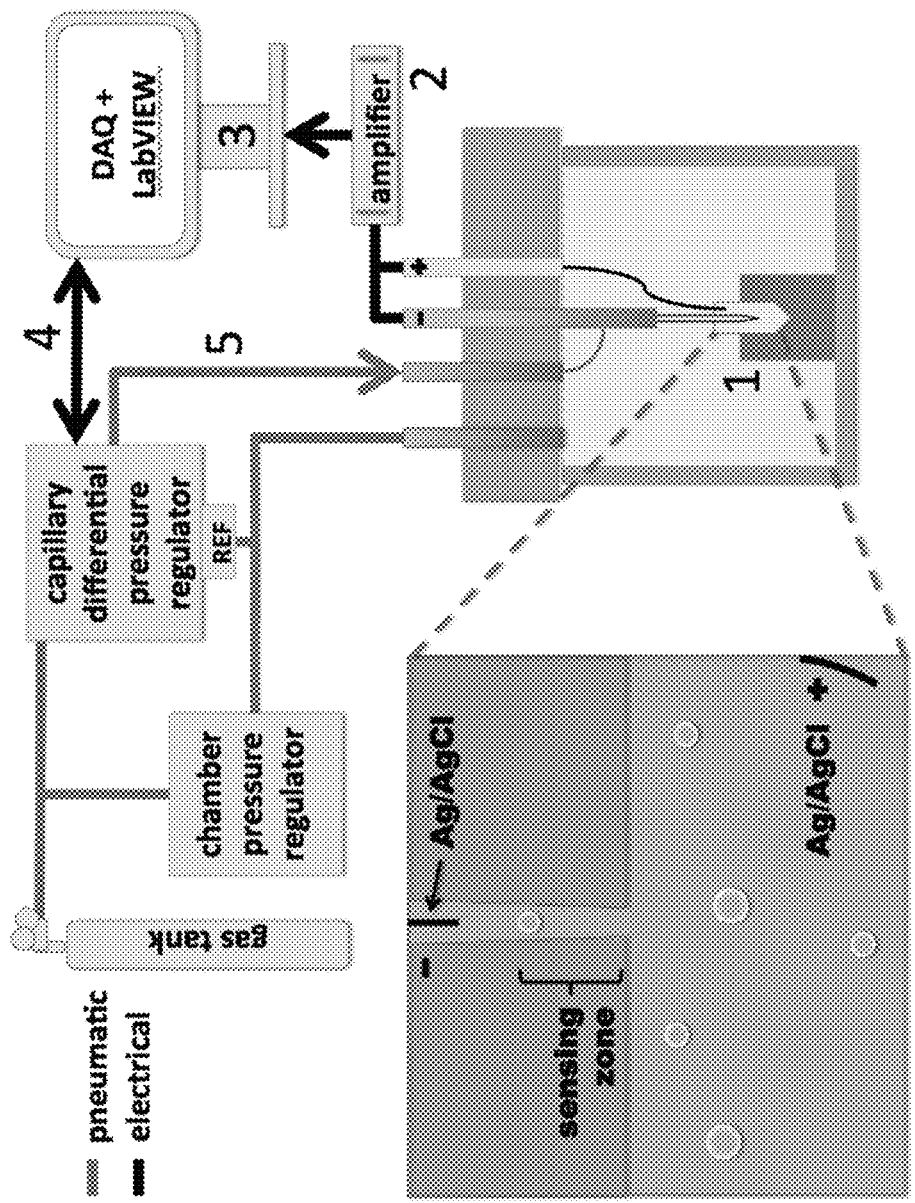
FIGS. 15A and 15B show, according to particular exemplary aspects, automated particle trapping and sizing systems.
Figure 15B:
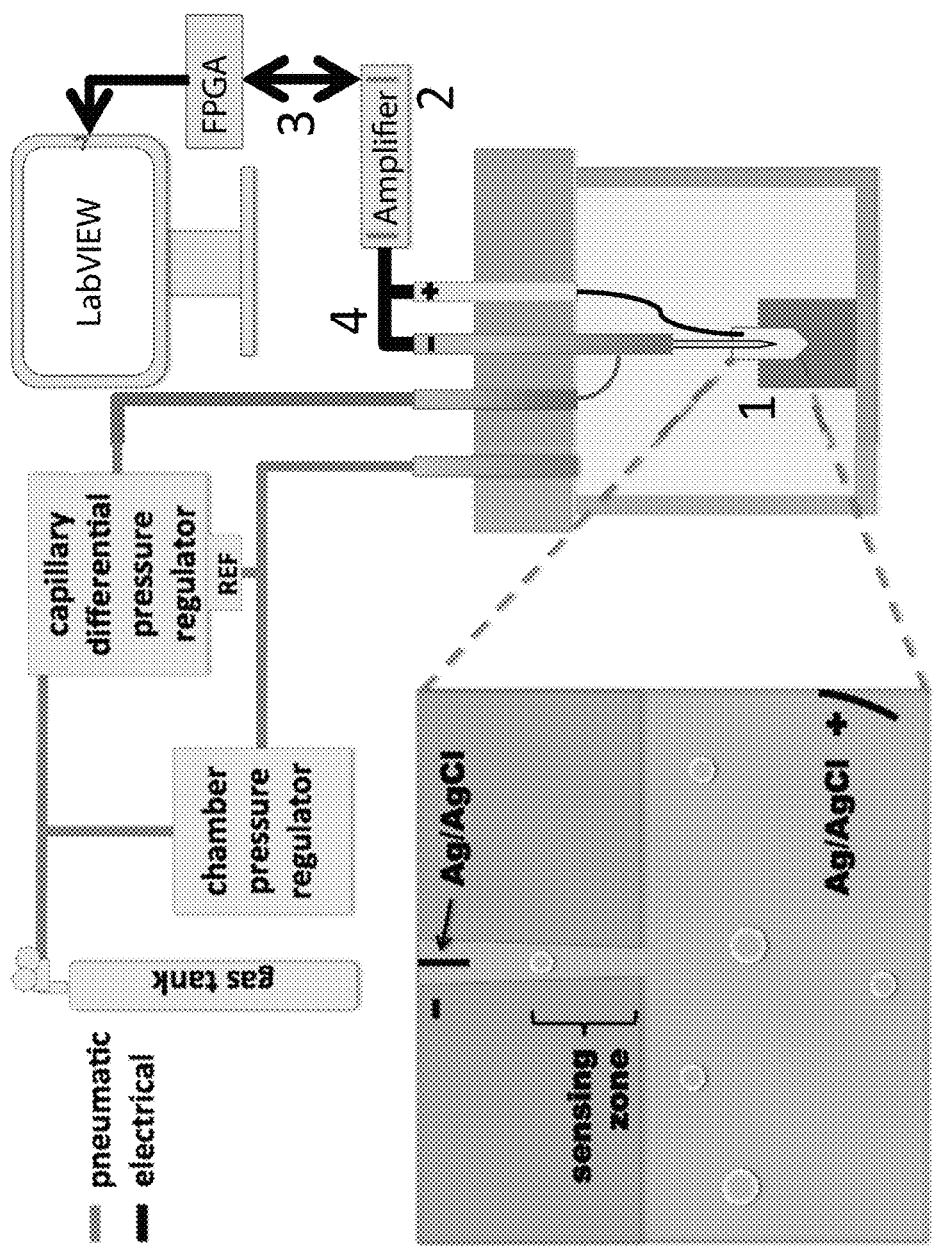

FIGS. 15A and 15B are diagrams showing, according to particular exemplary aspects of the present invention, an automated pressure-based trapping and particle sizing system and an automated voltage-based trapping and particle sizing system, respectively. These systems can be used for determining the size and/or shape of nanobubbles and nanoparticles in solution. For example, during translocation experiments, as described herein, a nanoparticle or nanobubble is captured across the sensing zone toward the proximal end by applying a differential pressure and/or a voltage across the sensing zone; upon detection of the resistive pulse caused by the translocation, the direction of the differential pressure or the voltage is reversed, thereby translocating the nanoparticle or nanobubble back across the sensing zone. This process is repeated a number of times over very short time intervals. The resulting resistive pulses caused by each translocation event are detected, for example by using computer-implemented data acquisition hardware and software, and used to determine a size and/or shape of the captured nanoparticle or nanobubble, with an increasing number of measurements providing increased accuracy. For example, the translocation processes can be repeated for as many cycles as desired, or until the particle is lost by diffusion. The use of many translocation events to gather a large data set relating to a single nanoparticle or nanobubble allows characterization of particles in a previously unattainable size range with greater accuracy than has been possible to date.

Example 1

Materials and Methods

Materials.

Spherical gold nanoparticles (diameter: 8 nm±7%, SD, measured by TEM) conjugated with a carboxy methyl polymer were purchased from Nanopartz, Inc. (Loveland, Colo.). Zeta potentials were measured as −51 mV and −15 mV (Nanopartz) and as −52 mV and −22 mV (Particle Characterization Laboratories, Inc., Novato, Calif.) in deionized water, and as −38 mV and −12 mV in 0.1 NaCl PBS pH 7.4 plus 0.1% Triton X-100 (Particle Characterization Laboratories, Inc.). Attempts to measure zeta potentials at higher salt concentrations yielded irreproducible values. The particles are denoted as −51 mV and −15 mV in the text even though ζ values are lower in salt solutions. Other materials included borosilicate glass micropipettes (OD: 1.5 mm, ID: 0.86 mm, Length: 10 cm, Sutter Instruments), hydrofluoric acid (48%), ammonium fluoride solution (~40%), ammonium fluoride etching mixture (AF 875-125, Sigma), pH 7.4 phosphate buffered saline (PBS) 10× (Invitrogen), 3M 12 micron Lapping Film (Ted Pella), Triton-X100 (Amresco), 0.25 mm Ag wire (World Precision Instruments), household bleach (5% hyprochorite) and sodium bicarbonate (Costco). Solutions were filtered through Millex-GP, 0.22 μm, polyethersulfone filters (Millipore).

Pipettes.

Pipettes were pulled with a Model P-1000 Flaming/Brown micropipette puller (Sutter Instruments) to a ~1 μm opening. Pulled pipette tips were then melted with a butane hand torch (flame tip positioned ~5 mm from the tip) for ~130 ms as the pipettes rotate by on a turntable at 3.5 cm/s. Sanding of the resulting terminal bulb was carried out by hand prior to microforge heating, which involved placing the pipette tip within a Ω-shaped platinum-iridium alloy filament (5 mm×5 mm) heating element made from a 5-mm wide platinum/iridium strip for ~400 ms. Pipette tips were initially imaged using an inverted Olympus IX50 microscope, and then a few were selected for imaging with a FEI Sirion SEM.

Glass Nanopore Fabrication.

Borosilicate glass micropipettes were heated at 600° C. for 12 h and then immediately sealed at both ends. After being pulled to ~1 μm opening, they were kept under a stream of dry nitrogen until the sharp tip was melted. The terminal bulb inclosing a conical cavity was then sanded to a flattened tip using fine sandpaper followed by microforge heating. Just prior to etching, the other end of the pipette was opened, fire polished, and backfilled with 1.0 M NaCl. Ag/AgCl electrodes where prepared by immersing an Ag wire in bleach for ~15 min prior to experiments, and were placed inside multiple pipettes connected in parallel as well as the etchant solution (a 1:2 dilution of 48% hydrofluoric acid in a ~40% ammonium fluoride solution). Pore formation was indicated by a jump in current measured using a Princeton Applied Research 2273 PARSTAT potentiostat operating in current vs. time mode with 250 mV applied potential. Pipette tips were immediately dipped into 3.0 M KOH for 10 s and transferred to a 1.0 M NaCl solution for current measurements. Pores having resistances between 100 and 200 MΩ were routinely made in this way, etched to larger sizes as needed by dipping briefly (15 s) into a 1:20 dilution of Ammonium fluoride etching mixture (AF 875-125), and repeating the etching process until threshold translocations no longer occurred.

Resistive Pore Sensing Measurements and Data Analysis.

Pipettes were placed into a BNC style electrode holder that allowed for application of pressure within the pipette (Warner Instruments), and current measurements made using a HEKA EPC-10 amplifier at a cutoff frequency of 3 kHz applied with a three-pole Bessel low-pass filter. PATCHMASTER data acquisition software was used to initially analyze and export current-time traces. A custom VBA Excel program was used to determine translocation peak parameters such as peak position, height, and width at half-height as a function of applied voltage. Each peak was inspected manually to ensure accurate measurements; in general, resistive pulses having a signal-to-noise ratio of less than 7:1 and/or a base width of less than 1 ms were excluded.

Finite-Element Simulations.

The finite-element simulations were performed using COMSOL Multiphysics 3.5 (Comsol, Inc.) on a high performance desktop PC.

Example 2

Micropipette-Based Glass Nanopores were Fabricated

Glass micropipettes were pulled to a ~1-μm opening and the pipette tips were then melted with a butane hand torch to produce a terminal bulb (FIG. 2A), similar to the method of Gao et al.[13] When applying etchant to the terminal bulb of a micropipette to expose the enclosed cavity, there is a tendency for a sharpened tip to form,[15] which can result in pore formation at points other than the tip. Wax coating of the sides of the tip has been used to avoid this problem,[13] but we found that we can exert better control over the etching process by taking steps to produce a flattened tip geometry prior to etching. To achieve this (FIG. 2B), the pipettes were sanded and the tip briefly remelted. Although sanding alone can be used to produce nanopores,[14] we have found inconsistent results with pores produced in this way. Speculating that sanding may introduce small cracks, we chose to stop sanding well before opening the pore. A setup with hydrofluoric acid etchant as the external solution was used to form a nano-scale pore in the sanded and remelted tip. Pore formation was detected by a spike in the current.

Figure 2A:
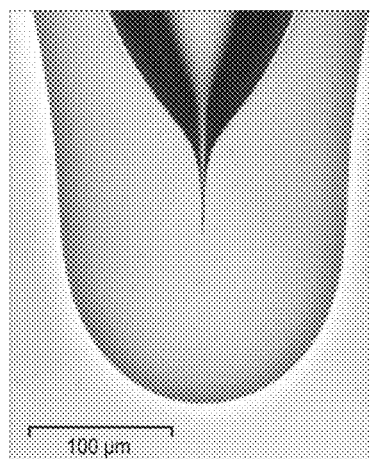
FIGS. 2A and 2B are, according to particular exemplary aspects, illustrations of the tip of a glass micropipette pulled, using a programmable micropipette puller, to form a narrow ~1-µm opening that was melted to produce a terminal bulb enclosing a cone-shaped cavity (A). The terminal bulb was sanded and briefly melted with a microforge to form a flattened geometry (dashed lines delineate the outlines of the original bulb shown in (A)). Ag/AgCl electrodes were placed across the unopened pore and hydrofluoric acid etchant was used as the external solution to form a nanoscale pore in the sanded and remelted tip (B). Pore formation was detected by a spike in the current.
Figure 2B:
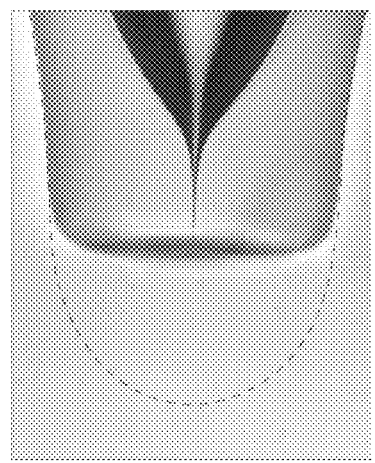

Specifically, FIGS. 2A and 2B are, according to particular exemplary aspects, illustrations of the tip of a glass micropipette pulled, using a programmable micropipette puller, to form a narrow ~1-μm opening that was melted to produce a terminal bulb enclosing a cone-shaped cavity (A). The terminal bulb was sanded and briefly melted with a microforge to form a flattened geometry (dashed lines delineate the outlines of the original bulb shown in (A)). Ag/AgCl electrodes were placed across the unopened pore and hydrofluoric acid etchant was used as the external solution to form a nano-scale pore in the sanded and remelted tip (B). Pore formation was detected by a spike in the current.

Example 3

Exemplary Micropipette-Based Glass Nanopores were Imaged

Glass micropipettes were prepared by a modification of the method described by Gao et al (*Anal. Chem* 81:80-86, 2009) (FIGS. 2A and 2B). Determining the size of GNPs is not simple. Indeed, others have reported being unable to image similar nanopores in the tip of glass pipettes using SEM (Vogel, R., et al., *Anal. Chem* 84:3125-3131, 2012; and Gao, C., et al., *Anal. Chem* 81:80-86, 2009). In particular aspects, for example, the pore size of one of our larger (70-nm) pores (FIG. 3) was measured. Based on the microscopic images (FIGS. 2A and 2B) and the characteristic asymmetric translocation profiles and FEA simulations, vide infra, the inner pore geometry is conical, with a ~2° cone angle (White & Bund, *Langmuir* 24:2212-2218, 2008).

Figure 3:
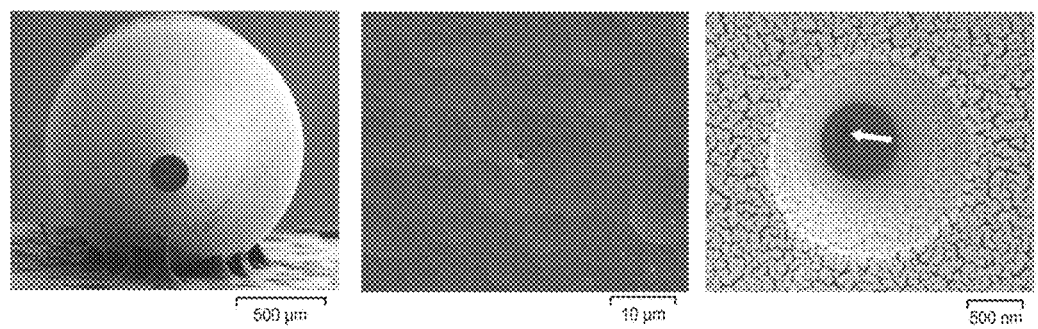
FIG. 3 shows, according to particular exemplary aspects, three Scanning electron microscope (SEM) images of the type of nanopore used in this study (this particular pore is larger than the ones used to detect 8-nm nanoparticles). A pipette having a resistance of 39 MO measured in 1.0 M NaCl was sputtered with an ~7 nm thick layer of gold prior to SEM imaging. The arrow in the lowest panel marks the location of the nanopore, which has a diameter of ~70 nm. Although these images show an external well surrounding the actual pore opening, we believe that, due to its large width, the well does not influence the nanopore-sensing zone.

Specifically, FIG. 3 shows, according to particular exemplary aspects, three Scanning electron microscope (SEM) images of the type of nanopore used in this study (this particular pore is larger than the ones used to detect 8-nm nanoparticles). A pipette having a resistance of 39 MΩ measured in 1.0 M NaCl was sputtered with an ~7 nm thick layer of gold prior to SEM imaging. The arrow in the lowest panel marks the location of the nanopore, which has a diameter of ~70 nm Although these images show an external well surrounding the actual pore opening, we believe that, due to its large width, the well does not influence the nanopore-sensing zone.

Example 4

Nanoparticles were Detected at the Threshold of the Pore Size

Identifying the size of a particle at the threshold of passing through the pore provides an alternative to SEM imaging for sizing micropipette-based GNPs. Experiments were performed to detect nanoparticle translocations using exemplary 8-nm diameter carboxy methyl polymer-coated Au nanoparticles having small standard deviation in size (±0.6 nm), at a typical concentration of 200 nM in a 1.0 M NaCl solution. Current vs. time (i-t) traces were recorded while a positive potential was applied to an Ag/AgCl wire electrode within the micropipette relative to the external solution. Very small pores (having a resistance between 100 and 200 MΩ, measured in 1.0 M NaCl) were initially produced, and repeatedly widened with dilute etchant until we detected pressure driven nanoparticle translocations (e.g., triggered by applying negative pressure within the pipette).

Figure 4A:
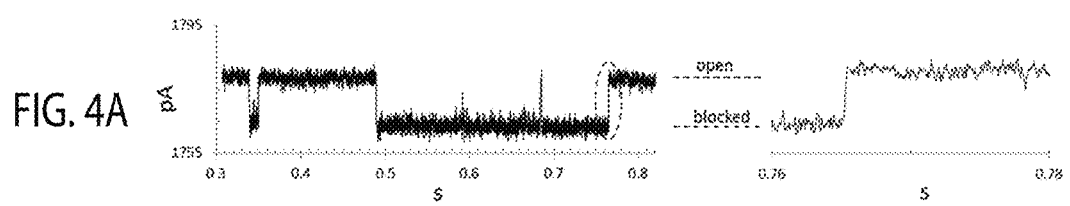
FIGS. 4A and 4B show, according to particular exemplary aspects, current versus time (i-t) traces used to determine when the Au nanoparticle size exceeds or is just at the threshold of the pore size.
Figure 4B:
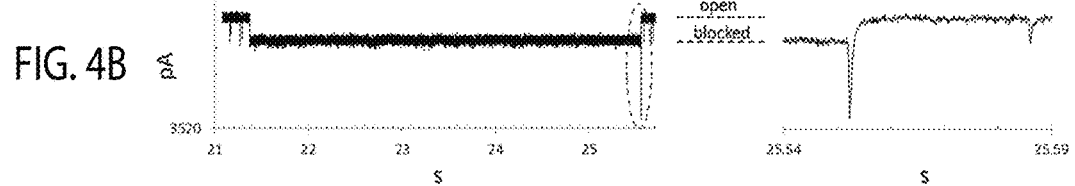

This approach enabled us to detect cases in which square blocks were terminated with a sharp spike at the end as illustrated by the 17 pA current block in FIG. 4B, which ends with a 70 pA peak before returning to the base current. Since this terminal spike is large and has characteristics of a typical translocation, it likely represents a particle passing through the pore after an initial partial blockade of the opening. Vercoutere et al. observed similar long shallow blockades caused by individual hairpin DNA molecules prior to a rapid deep blockage indicating translocation of the DNA through an α-hemolysin pore (Vercoutere, W., et al., *Nature Biotechnology* 19:248-252, 2001). Though the geometrical considerations for gold nanoparticles are much simpler, it is possible that the particle coating requires time to compress in order for the particle to fit through the pore at the threshold size. Gao et al., also used the threshold condition to estimate the size of their pores using DNA, 10-nm gold nanoparticles, and even single molecules of β-cyclodextrin, based on simple square-shaped blocks lacking a terminal spike (Gao, C., et al., *Anal. Chem* 81:80-86, 2009). Based upon repeated observations of this kind, it is concluded that the occurrence of square blockages without a sharp spike at the end represent transient blockages, FIG. 4A, of the nanopore orifice by the Au nanoparticles, but without successful translocation.

FIGS. 4A and B show, according to particular exemplary aspects, current versus time (i-t) traces used to determine when the Au nanoparticle size exceeds or is just at the threshold of the pore size. In these experiments, 8-nm Au nanoparticles (ζ=−51 mV) were placed in the external solution, and a pressure of ~0.5 atm and voltage of 250 mV were applied to drive the particles into the nanopore. (A) Square-shaped blockades of widely varying duration are observed when the particle size exceeds the pore size. The current within these blocks sometimes increases briefly, as seen at 0.59 s and 0.68 s, but eventually returns to the base current level as seen in the dashed oval in (A) (the trace on the right is an expansion of this region). (B) When the particle is at the threshold of the pore size it will eventually pass through the pore accompanied by a large current spike (dashed oval in (B)). Note that this current spike (expanded on the right) has the asymmetric shape characteristic of a typical translocation through a conical pore. The 1.0 M NaCl solution was buffered at pH 7.4 with 7 mM $Na_2HPO_4$, 21 mM $KH_2PO_4$, and contained 0.1% Triton X-100.

Example 5

Particle Capture and Release by Applied Pressure was Demonstrated

Figures 9A, 9B:
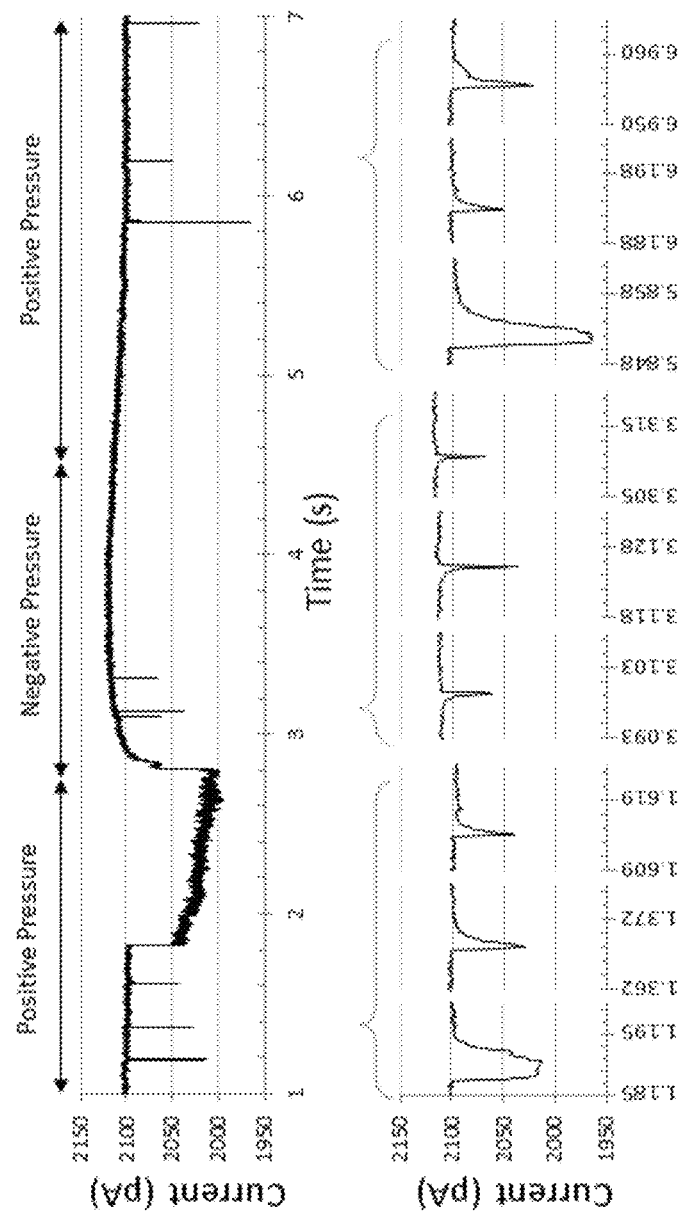
FIGS. 9A and 9B show, according to particular exemplary aspects, forward and reverse translocation of three nanoparticles as a function of the applied pressure (current versus time traces for three nanoparticles reversing direction due to applied pressure).

According to particular aspects, applying pressure within the pipette offers considerable control over nanoparticle translocation, including the ability to draw individual particles into the pore and push them out again repeatedly, as illustrated in FIGS. 9A and 9B. Because the quasi-triangular peak shape depends on the direction of translocation, these experiments provide confirmation that the present exemplary pores are conically shaped and open inwardly. Observations of particle reversal with application of pressure have been used to measure the size of individual particles depending upon their recapture probability (Lan & White, *ACS Nano* 2012, 6, 1757-1765, 2012). In the present experiment, the distinct differences seen in translocation shape for individual particles reflect the acute sensitivity of this technique to monitor subtle nanopore/nanoparticle characteristics that are most likely based on geometrical and charge interactions.

FIGS. 9A and 9B show, according to particular exemplary aspects, forward and reverse translocation of three nanoparticles as a function of the applied pressure (e.g., current versus time (i-t) traces for three nanoparticles reversing direction due to applied pressure). A nanopore having a resistance of 117 MΩ measured in 1.0 M NaCl was used to observe 8-nm gold nanoparticles under constant applied potential (250 mV). In (A), three particles enter the pore between 1.2 and 1.6 s as negative pressure (−0.25 atm) is applied to the pipette. A pore block between 1.8 and 2.8 s is removed by applying positive pressure (0.5 atm), pushing the three particles back out of the pipette between 3.1 and 3.3 s. A negative pressure (−0.25 atm) is then applied at 4.5 s to draw the three particles back through the nanopore between 5 s and 7 s. Although the standard deviation in the particle size distribution was only ±0.6 nm, distinct peak shapes seen in the i-t expansions (B) reflect subtle differences in the particle sizes, and allow identification of individual particles. The applied positive pressure between 3.1 and 3.3 s was greater than the applied negative pressures resulting in increased translocation velocity and therefore narrower peak widths.

Example 6

Particles were Captured and Released by Applied Potential

According to additional aspects, FIGS. 5A-5D demonstrate that varying the applied potential can also be used to drive particles into and out of a pore repeatedly.

FIGS. 5A, 5B, 5C, and 5D illustrate, according to particular exemplary aspects, i-t traces showing a single nanoparticle repeatedly going in and out of a nanopore as the applied potential is reversed. A voltage square wave oscillating at 10 Hz between +1000 mV and −1000 mV is shown in (A) with circled portions indicating where translocations occur in the experimental traces (B) (resistive pulses in the i-t trace shown in (B)). The i-t traces in (B) are clipped to show just the relevant 50-ms portions of the square wave where translocations occur. In (D), a particle reverses direction (single nanoparticle passing back and forth through the pore orifice) for a square wave oscillating at 3 Hz between only +525 and +225 mV (C). Both solutions contained 8-nm gold nanoparticles (ζ=−51 mV) in 1.0 M NaCl PBS pH 7.4 plus 0.1% Triton X-100. Particle concentration for the experiment in (B), equals 50 nM, and in (D) equals 320 nM.

In the experimental results shown in FIGS. 5A and 5B, no pressure was applied to the pipette, but instead the particle motion followed a 10 Hz square wave varying between +1.0 V and −1.0 V. The four occasions of a particle going into and out of the pore were preceded and followed by several seconds without any particle translocations, indicating that repeated translocations of a single particle were observed. Voltage switching experiments have been used to recapture individual DNA strands (Gershow & Golovchenko, *Nature Nanotech* 2:775-779, 2007). The results shown in FIGS. 5C and 5D demonstrate that even a small change in the amplitude of applied potential (between only +225 mV to +525 mV) is sufficient to drive particles into and out of a pore.

According to further aspects, note that the resistive pulse asymmetry in these experiments is opposite from what would be expected based upon electrophoresis, implying that electroosmosis is the dominant force.

Example 7

Nanoparticle Dynamics were Controlled by Applied Pressure and Applied Potential; Taking Advantage of Electroosmosis and by Applying a Constant Pressure to Shift the Zero Velocity Point to a Potential with Acceptable Signal-to-Noise Ratio Either electrophoresis or applied pressure alone has typically been used as the driving force for moving nanoparticles through a nanopore and demonstrated in the previous section. Decreasing the particle translocation velocity by lowering voltage has limitations, however, because the signal-to-noise ratio is reduced dramatically as the voltage decreases. Here we report fine control of particle velocities by taking advantage of electroosmosis and by applying a constant pressure to shift the zero velocity point to a potential with acceptable signal-to-noise ratio (FIGS. 6A and 6B).

Figure 6A:
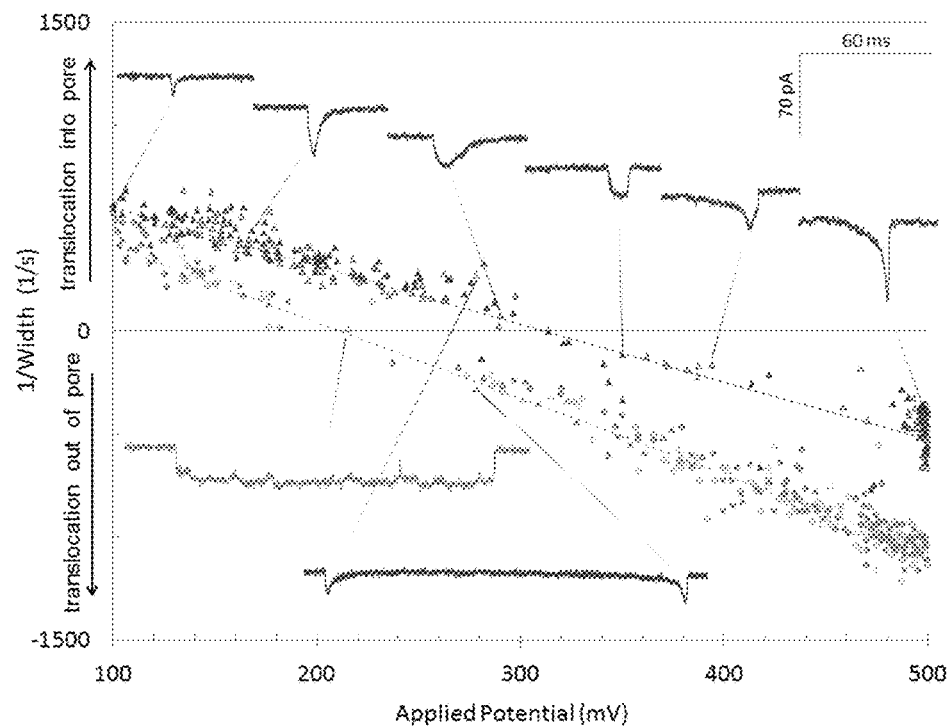
FIGS. 6A and 6B show, according to particular exemplary aspects, nanoparticle translocation velocity vs. applied voltage under −0.047 atm (A) and −0.35 atm pressure (B).
Figure 6B:
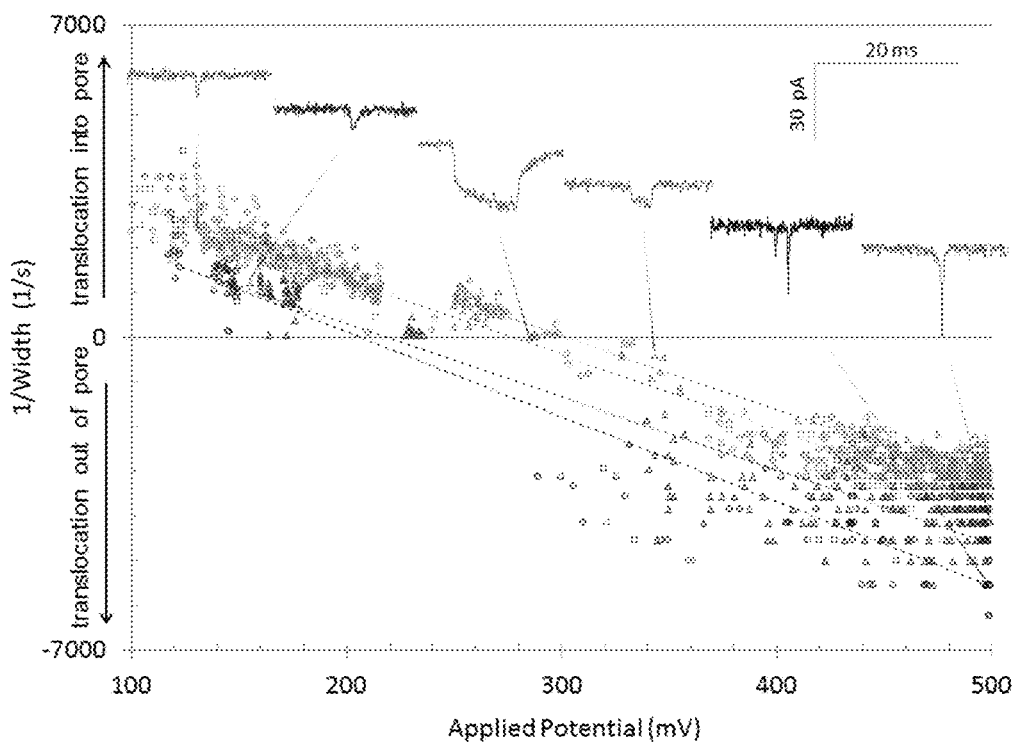

FIGS. 6A and 6B show, according to particular exemplary aspects, nanoparticle translocation velocity vs. applied voltage under −0.047 atm (A) and −0.35 atm pressure (B). The solution conditions are for (A): 1.0 M NaCl, open and filled red triangles ($\zeta$=−51 mV) and open and filled blue circles ($\zeta$=−15 mV), and for (B): 0.2 M NaCl: open orange triangles ($\zeta$=−51 mV) and open blue circles ($\zeta$=−15 mV); 0.1 M NaCl: open black triangles ($\zeta$=−51 mV) and open black circles ($\zeta$=−15 mV); all solutions were buffered at pH 7.4 with 7 mM $Na_2HPO_4$, 21 mM $KH_2PO_4$, and contained 0.1% TritonX-100. Filled and open symbols in (A) represent two consecutive dataset collected under identical conditions. Dashed lines through data points represent second order polynomial fits. Representative i-t traces for particular translocations at different voltages are shown. The insets illustrate current-time (i-t) traces for particular data points; the scales for the traces in (A) and (B) are indicated in the upper right of each panel.

In this experiment, translocation velocities were assumed to be proportional to the inverse of the peak width at half height, with positive values indicating translocations into the pipette. Negative pressures indicate fluid flow into the pipette; positive voltages are measured relative to the external solution (see FIG. 1). At the outset of the experiment, the majority of 8-nm gold particles were outside of the pipette, except for a small number of particles that had been pulled into the pipette under vacuum just prior to the experiment. The pipette was then subjected to a constant negative pressure (−0.047 atm in FIG. 6A and −0.35 atm in FIG. 6B) and +500 mV. Both of these forces should act to drive negatively charged particles into the pipette, and yet the particle translocation profiles clearly indicated that nanoparticles were expelled from the pipette.

According to particular aspects, this is explained by the presence of a large electroosmotic flow (EOF) that overpowers both the applied pressure and the electrophoretic forces (EPF) acting on the particles under these conditions (FIG. 1).

With reference to FIG. 6, as the potential was ramped down to +100 mV over the course of 5 minutes, the EOF decreased at a faster rate than the EPF and driving forces acting on the particle were balanced at a characteristic transition voltage that was determined by the zeta potential of the particles. Particle velocities, measured as the peak widths at half height, were markedly reduced at this transition. Of the 1,890 translocations shown in FIGS. 6A and 6B, thirteen had peak widths greater than 20 ms and two were as large as ~200 ms. For the slowest translocations, the negation of all particle driving forces allowed us to see the effects of Brownian motion as the particle flickered in and around the sensing zone (blue trace inset in FIG. 6A). This is in sharp contrast to the outer portions of the figure where peak widths were ≤0.2 ms, representing an increase in particle velocity of 3 orders of magnitude. The limited number of translocations near 200-300 mV is a consequence of the diminishing particle rate of entry near the transition voltage and of the small number of particles initially inside the pipette, the particles were eventually exhausted as the potential was decreased from 500 mV to the transition voltage. Below this voltage, particles were drawn into the pipette from the external solution, as the combined EPF and applied pressure force became larger than the EOF.

Figure 7:
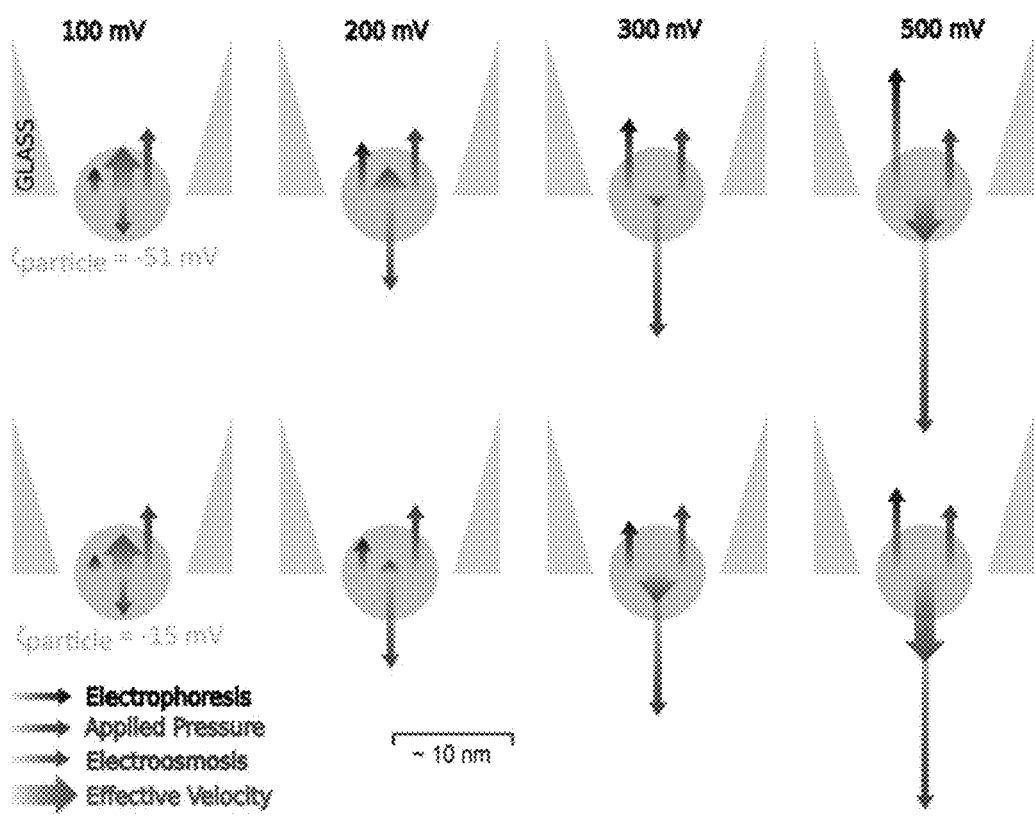
FIG. 7 illustrates, according to particular exemplary aspects, the contributions to the effective velocity made by the applied pressure, electrophoresis ($v=\in/\eta\xi_{particle}E$) and electroosmosis ($v=-\in/\eta\xi_{pore}E$) for the experiments represented in FIG. 6A.

FIG. 7 illustrates the contributions to the effective velocity made by the applied pressure, electrophoresis ($v = \in / \eta \xi_{particle} E$) and electroosmosis ($v = -\in/\eta\xi_{pore}E$) for the experiments represented in FIG. 6A. Specifically, FIG. 7 schematically shows, according to particular exemplary aspects, controlling nanoparticle velocity in conical nanopores. The experiments presented in FIG. 6A are explained in terms of force contributions to the effective velocities on each type of nanoparticle, where the voltage-dependent peak widths presented in FIGS. 6A and 6B result from the summed contributions of different forces acting on the charged nanoparticle. The applied pressure (−0.047 atm) remains constant throughout all measurements, but the particle-dependent electrophoretic and particle-independent electroosmotic forces change at different rates with varying voltage. As a result, the $\zeta$=−51 mV particles reach a minimum velocity near 300 mV while the $\zeta$=−15 mV reach a minimum velocity near 200 mV.

Example 8

Factors Governing Particle Velocity

In resistive pulse sensing, particle velocities are governed by the relative strengths of the EPF, EOF, and applied pressure. While EPF is a function of the charge of the particle, the EOF is only dependent upon the charge of the pore, and therefore the two forces increase with the applied voltage at different rates. Furthermore, these forces have different dependencies on pore geometry. Increasing the channel-like character of conical pores spreads the electric field over a larger sensing zone, which would be expected to reduce EPF. By contrast, increased pore channel length has been observed to increase the EOF.[10,19] Though the geometry of the GNPs used in this study are conical, they have significant channel-like character due to the small cone angle (~2°; e.g., selected from among: 2°±0.1°; 2°±0.2°; 2°±0.3°; 2°±0.4°; 2°±0.5°; 2°±0.6°; 2°±0.7°; 2°±0.8°; 2°±0.9; 2°±1.0°, and, according to particular aspects of the present invention, this is important in achieving the delicate balance of the forces controlling particle dynamics.

Without pressure, the minimum in particle velocity occurs at zero voltage. By applying suitable pressure, we are able to shift the minimum velocity point to a voltage range that is convenient, and that has substantial utility for measurements. Thus, for a particular pipette, we applied a pressure necessary to place the transition voltage in this range; that is, the voltage at which particle velocities are minimized due to equivalence of the forces drawing particles into the pore (primarily the EPF and fluid flow caused by applied pressure) and those driving particles out of the pore (primarily the EOF). Firnkes et al. were able to balance the EPF and EOF by finding a pH at which the zeta potential of the pore and the molecule studied were equal.[10] However, simply eliminating the driving force does not allow for general control of particle dynamics. For the conical pores used in this study, the EOF appears to increase with voltage at a greater rate than the EPF, and we observed translocations in the opposite direction of electrophoresis under atmospheric conditions. Zhang et al. also demonstrated DNA translocating in the opposite direction of electrophoresis and attributed this to a large EOF.[11] In the experiments in FIGS. 6A and 6B we took advantage of the large change in EOF with respect to voltage, and were able to control the entire range of particle velocities from near zero to the limit of the electronic bandwidth filtering of the amplifier (10 kHz), in both the inward and outward direction and between +100 and +500 mV.

Example 9

The Effects of Salt Concentration and Particle Charge on Nanoparticle Dynamics Experiments in 0.1M and 0.2M NaCl solutions required a much larger applied pressure (−0.35 atm) than those in 1M NaCl (−0.047 atm); the data are presented on a separate graph to accommodate a sufficiently wide range of particle velocities (FIG. 6B). The need for higher pressure would be expected from the longer Debye lengths at lower salt concentrations, which generate significantly larger EOFs along the pore surface. Since the EOF at the transition voltage is larger than the applied pressure, we can say that pressures greater than 0.3 atm are generated in 0.2M NaCl at 250 mV, and in 0.1M NaCl comparable pressures are generated at 180 mV. By contrast, Takamura et al. reported the fabrication of "extremely high pressure" electroosmotic pumps of 0.05 atm under tens of volts.[23]

Examining the velocities of differently charged particles at a particular combination of salt concentration and applied voltage reveals the effect of particle charge. Under these conditions, the applied pressure and EOF are identical, and therefore the remaining electrophoretic force decreases the velocity of negative particles moving out of the pore and increases their velocities as they move in. This explains why the velocity trend lines for the more highly charged ($\zeta=-51$ mV) particles were always above those for the less highly charged ($\zeta=-15$ mV) particles (FIGS. 6A and 6B). It should be noted that the 0.1M NaCl velocities fall below the 0.2M NaCl due to an increased EOF and not because of charge effects.

Example 10

Factors Affecting Resistive Pulse Peak Shape

It is well known that the path of a particle through a conical nanopore determines the shape of a resistive pulse event. Inhomogeneity of the electric field within the sensing zone due to a stronger field near pore walls has been shown to cause as much as a 15% deviation in peak amplitude for particles that do not travel straight through the center of the pore (off-axial translocations).[20] Interaction of particles with pore walls can also lengthen translocation times, a factor that must be taken into account for analysis based upon peak widths.[9] The ability to slow particle velocity to a degree achieved in our experiments allows a closer examination of the factors that affect translocation kinetics. This is illustrated by the insets in FIGS. 6A and 6B, which demonstrate clear peak shape differences during the course of translocations. In particular, we have observed the steep side of a typical asymmetric translocation exhibiting biphasic character to differing degrees (compare the rightmost inset translocation with both the second and the fifth from right). These stages of resistance change may be explained by contributions from an inhomogeneous electric field, pore wall interactions, diffusion, and/or possibly a second EOF that arises from the double layer associated with the particle itself. An additional complicating factor would be if our pores were not entirely smooth throughout the sensing zone, although the observation of numerous "ideally shaped" translocations[21] argues against this possibility.

Example 11

Velocity Measurement Limitations

Although there was considerable data scatter, the general trend was reproducible across two independent experiments carried out under identical conditions (FIG. 6A, opened and closed symbols). The experiments in FIG. 6A were carried out with the same pipette (having a resistance of 110 MΩ at 1M NaCl), and those in FIG. 6B were all carried out with a different pipette. Some of the data scatter at highest and lowest applied potential is based on limitations in our ability to accurately measure peak width for the fastest moving particles (thus the digitization seen on the right of FIG. 6B). Slow moving particles also involve scatter, presumably because additional surface forces acting on the particles become significant under these conditions. The data scatter is particularly severe when the salt concentration is <0.2M NaCl, mostly due to the relatively poor signal-to-noise. The experiments under low salt conditions (0.1-0.2M NaCl) were done with a pore within 10 MΩ (measured at 1M NaCl) of the threshold size in order to maximize the amplitude of the resistive pulses, particularly near 100 mV. The observation of several near zero velocity events that do not fall in line with the data trend likely indicates particles that interacted strongly with the pore wall, because fluid flow was not fast enough to deter physisorption.

One additional source of apparent data scatter is cross contamination between experiments. For example, the $\zeta=-15$ mV data shown in FIG. 6A was collected prior to the $\zeta=-51$ mV data shown in the same figure, and despite efforts to thoroughly rinse the pipette between experiments the red triangles falling in line with the $\zeta=-15$ mV data likely indicates the presence of residual $\zeta=-15$ mV particles. This assumption is supported the fact that the signals show the opposite peak symmetry at the transition voltage of the $\zeta=-51$ mV particles. This is demonstrated by the lowest red inset in FIG. 6A, which suggests that two particles, one with $\zeta=-15$ mV and one with $\zeta=-51$ mV, are crossing the pore in different directions at the same applied potential.

In summary, according to particular aspects, the dynamics of 8-nm nanoparticle translocations, and nanobubble translocations, through micropipette GNPs can be controlled, and we demonstrated control over the interplay of electrophoretic (EPF), electroosmotic (EOF) and pressure forces by balancing translocation velocity as a function of particle charge, salt concentration, and applied pressure. Detection and characterization of nanoparticles and nanobubbles has a growing number of applications across different disciplines, from research and diagnostics, drug delivery, detection of nanoparticle waste released by industrial nanotechnology applications, and bio-sensing. Overcoming the problem of excessive particle or bubble velocities through appropriate choice of nanopores and observation parameters is an important step toward applying these technologies. Controlling nanoparticle and nanobubble dynamics allows nanopore sensing to advance from mere detection of nanoparticles into the realm of nanoparticle characterization in a previously unattainable range.

Example 12

Finite Element Analysis (FEA) Simulations were Performed

Finite-element simulations using COMSOL Multiphysics were performed to provide a more quantitative description of the experimental results at each of the salt concentrations studied. We used a quasi-steady method which assumes that the fluid and particle are in equilibrium.[20-22] Based on the assumption that the sum of the hydrodynamic drag and electrokinetic forces on the nanoparticle (or nanobubble) are zero, the velocity of the particle or bubble may be iteratively determined using the Newton-Raphson method to solve the following equations from an appropriate initial guess.

A quasi-steady force balance is expressed as:

$$F_{total} = F_H + F_E = 0 \quad (1)$$

where $F_H$ and $F_E$ are hydrodynamic force and electrokinetic force exerted on the particle, respectively. These forces are given by eqs (2) and (3):

$$F_H = \int (T_H \cdot n) dS \quad (2)$$

$$F_E = \int (T_E \cdot n) dS \quad (3)$$

where $T_H$ and $T_E$ are the hydrodynamic stress tensor and the Maxwell stress tensor, respectively, n is the unit normal vector, and S represents the surface of nanoparticle.

The Navier-Stokes equation describes the laminar flow of the incompressible fluid.

$$u \nabla u = \frac{1}{\rho}\left(-\nabla p + \eta \nabla^2 u - F\left(\sum_i z_i c_i\right) \nabla \Phi\right) \quad (4)$$

In eq 4, u and $\Phi$ are the local position-dependent fluid velocity and potential, $c_i$ and $z_i$ are concentration and charge of species i in solution, p is the pressure and F is Faraday's constant. The solution density $\rho=1000$ kg/m³ and the dynamic viscosity $\eta=0.001$ Pa*s, respectively, correspond approximately to the aqueous solution. The particle velocity u corresponds to the boundary velocity between the particle surface and surrounding fluid, eq 4.

The ion distribution and potential profile in the system are modeled by the Nernst-Planck-Poisson equations as below:

$$J_i = -D_i \nabla c_i - \frac{F z_i}{RT} D_i c_i \nabla \Phi + c_i u \quad (5)$$

$$\nabla^2 \Phi = -\frac{F}{\varepsilon} \sum_i z_i c_i \quad (6)$$

In eq 5, $J_i$ and $D_i$ are the ion flux vector and diffusion coefficient of species i in solution, respectively. $D_{Na}^+ = 1.33 \times 10^{-9}$ m²/s and $D_{Cl}^- = 2.03 \times 10^{-9}$ m²/s. The absolute temperature T=298 K, and the gas constant R=8.314 J/K. $\varepsilon$ is the dielectric constant of 78.

Figure 8A:
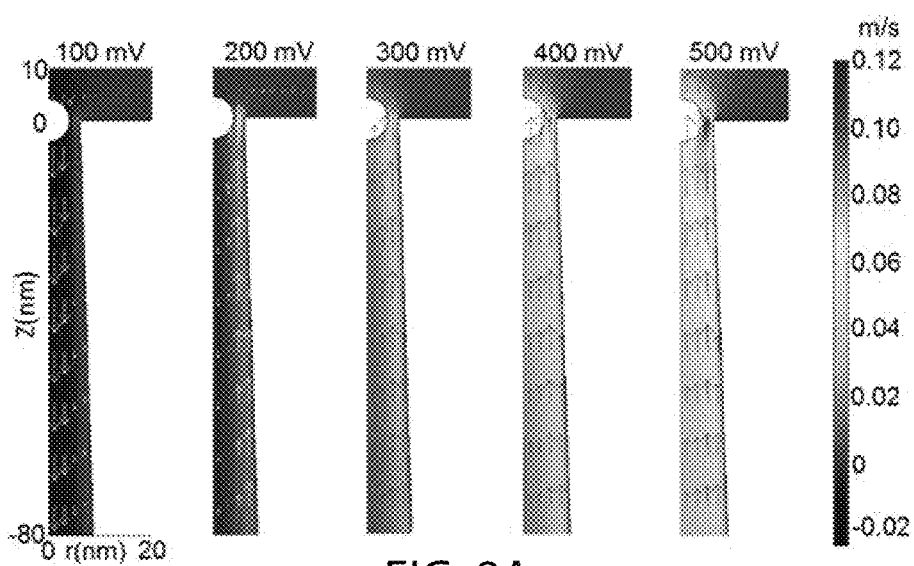
FIGS. 8A, 8B, and 8C illustrate, according to particular exemplary aspects, (A) simulated velocity profile for a nanoparticle ($\zeta=-15$ mV) in a 0.2 M NaCl solution, at 0.35 atm pressure and applied voltages between 100 and 500 mV corresponding to the turquoise lines in FIG. 6B and FIGS. 8C. (B) and (C) are plots of particle velocities corresponding to the data in FIGS. 6A and 6B, respectively. The data point colors and symbols follow the same scheme used to plot experimental data in FIGS. 6A and 6B. Parameters and other details of the finite-element simulation are presented in the SI file.
Figure 8B:
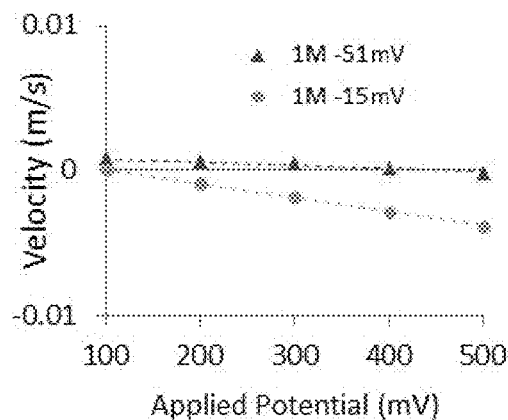
Figure 8C:
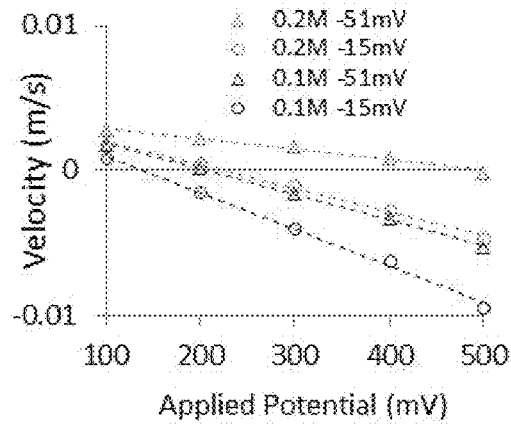

FIGS. 8A-8C present results of the FEA simulations corresponding to the experiments in FIGS. 6A and 6B. FIG. 8A shows velocity profiles and streamlines along the pore axis corresponding to the experimental conditions (zeta potential $\zeta = -15$ mV, 0.2 M NaCl and 0.35 atm external pressure) in FIG. 6B (light blue line). Using a cone angle of 1.87°, the general trends seen in the experiment were reproduced, with particles entering the pore at 100 mV, exiting the pore at 500 mV, and a crossover point occurring at ~200 mV (simulated) and ~250 mV (experimental).

Figure 8D:
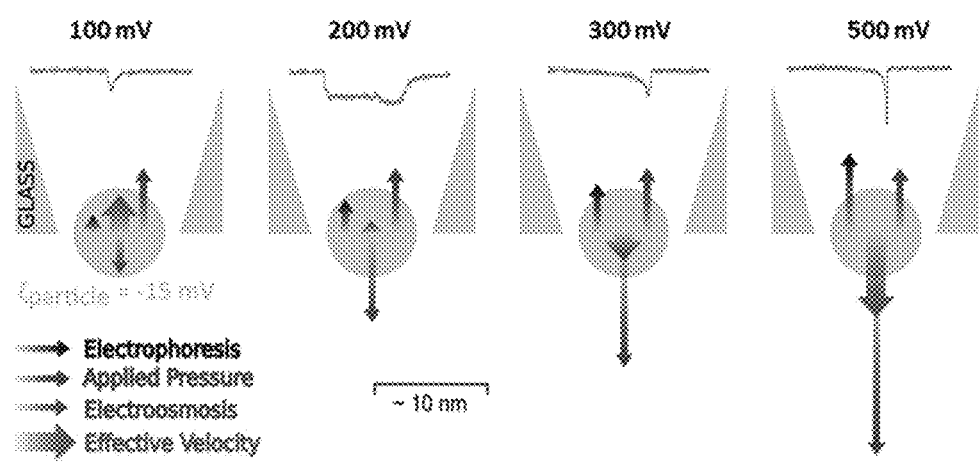
FIG. 8D illustrates, according to particular exemplary aspects, the contributions to the effective velocity made by the applied pressure, electrophoresis ($v=\in/\eta\xi_{particle}E$) and electroosmosis ($v=-\in/\eta\xi_{pore}E$) for a $\zeta=-15$ mV nanoparticle.

In FIGS. 8B and 8C, simulation parameters were varied to reproduce the velocity trends seen in FIGS. 6B and 6A, respectively, for the differently charged particles at varying salt concentrations. A better quantitative match with experimental results is seen at the lower salt concentrations (FIG. 8B). Specifically, the same velocity trends are seen as particle charge and the ionic strength of the solution are varied, with velocity reversal occurring in the applied voltage between 100 and 500 mV range. At higher salt concentration (FIG. 8C) the agreement with the experimental measurements is weaker, but still qualitatively capture the trend in the experimental results. Given the approximations in the modeling parameters and the uncertainty in the nanopore geometry, the governing equations employed in the FEA simulations provide a very satisfactory description of the particle motion. FIG. 8D illustrates, according to particular exemplary aspects, the contributions to the effective velocity made by the applied pressure, electrophoresis ($v = \varepsilon/\eta \xi_{particle} E$) and electroosmosis ($v = -\varepsilon/\eta \xi_{pore} E$) for a $\zeta = -15$ mV nanoparticle.

FIGS. 9A and 9B show forward and reverse translocation of three nanoparticles as a function of the applied pressure. A nanopore having a resistance of 117 MΩ measured in 1 M NaCl was used to observe 8-nm diameter Au nanoparticles at constant applied potential (250 mV). In (A), three particles enter the pore between 1.2 and 1.6 s as negative pressure (−0.25 atm) is applied to the pipette. A pore block between 1.8 and 2.8 s is removed by applying a positive pressure (0.5 atm), pushing the three particles out of the pipette between 3.1 and 3.3 s. A negative pressure (−0.25 atm) is then applied at 4.5 s to draw the three particles back through the nanopore between 5 s and 7 s. Although the standard deviation in the particle size distribution was only ±0.6 nm, distinct peak shapes seen in the i-t expansions shown in (B) reflect subtle differences in the particle sizes, and allow identification of individual particles. The applied positive pressure was greater than the applied negative pressures resulting in increased translocation velocity and therefore narrower peak widths.

Surface Charge Density of the Au Nanoparticle Estimated from the Zeta Potential in an Extremely Diluted Electrolyte Solution.

Figure 10:
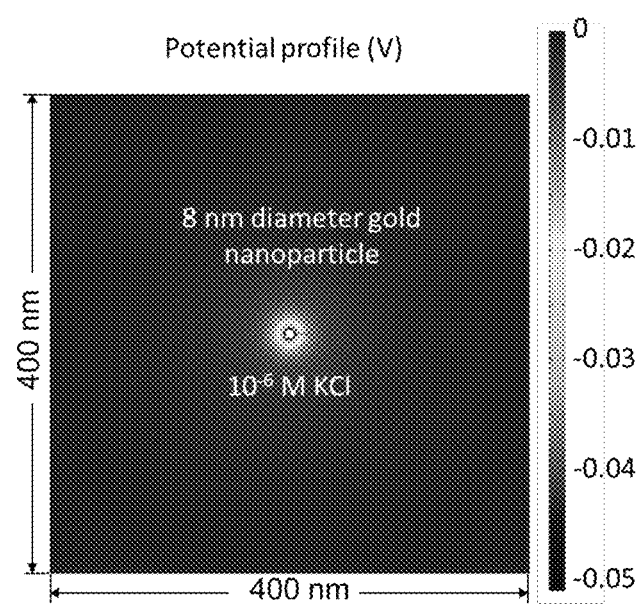
FIG. 10 shows a simulated potential profile generated by a −9 mC/m$^2$ charged Au nanoparticle with a diameter of 8 nm.

The effective surface charge of the Au nanoparticles was estimated by finite-element simulation, assuming that the simulated surface potential is equal to the measured zeta potential. Experimentally, the zeta potential of nanoparticle was measured in deionized (DI) water which contains ~10⁻⁷M hydroxide (OH⁻) and hydronium ion (H₃O⁺) due to water's self-dissociation. Considering trace ions remain in the DI water, the electrolyte was set as $10^{-6}$ M KCl in the simulation. An arbitrary surface charge density was initially set on the Au nanoparticle surface, and then Poisson and Nernst-Planck equations were iteratively solved to obtain a surface charge density value, which yields a surface potential within 10% of the measured zeta potential. A surface charge density of −3 and −9 mC/m² were obtained which produces a simulated surface potential of −17.0 and −51.0 mV, respectively, compared with measured −15 and −51 mV. FIG. 10 shows the simulated potential profile generated by a −9 mC/m² charged gold nanoparticle with a diameter of 8 nm.

The Geometry and Boundary Conditions for a Simulation of the Particle Velocity in 0.1 and 0.2 M NaCl Solutions.

In the simulation, 0.35 atm pressure and −0.1 to −0.5 V voltage were applied across the nanopore, corresponding to experimental values. An 8-nm diameter gold nanoparticle was placed at the nanopore orifice, z=0 and r=0, whose surface charge density was chosen as −3 or −9 mC/m², corresponding to a zeta potential of −15 and −51 mV. The determination of the nanoparticle surface charge density was detailed in SI 2 above. A mesh size <0.5 nm was used at the nanopore's charged surface (red line highlighted) as well as the nanoparticle surface, which is sufficient to resolve the electrical double layer.

Figure 11:
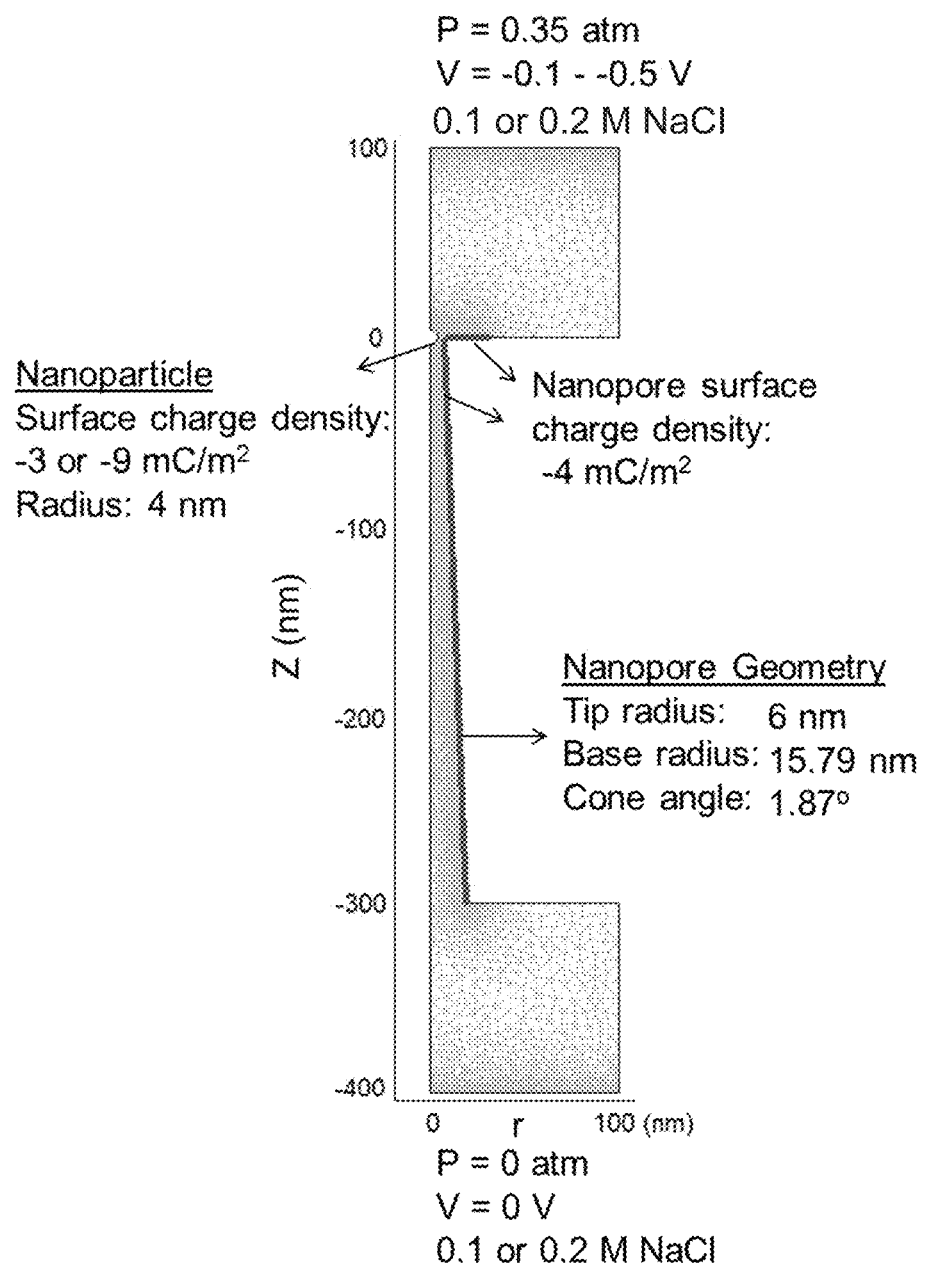
FIG. 11 shows geometry and boundary conditions for the finite-element simulation in a 0.1 M or 0.2 M NaCl solution and P=0.35 atm.

The nanopore surface charge density and geometry were estimated based on the nanopore ion current and ion current rectification ratio, defined as the ratio of currents at −500 and 500 mV (inside vs. outside nanopore). In 0.1 M NaCl, a nanopore surface charge density of −4 mC/m² produces a simulated rectification ratio of ~1.13 while the experimental value is ~1.2; the simulated current at 500 mV is 550 pA, while the experimental value is 600 pA. FIG. 11 shows the geometry, mesh and boundary conditions used in the simulation.

The Geometry and Boundary Conditions for a Simulation of the Particle Velocity in 1 M NaCl Solution.

The boundary conditions and mesh setting were the same as in the example of FIG. 11, except that the pressure was decreased to 0.047 atm and the bulk salt concentration was increased to 1 M, corresponding to experimental parameters.

Figure 12:
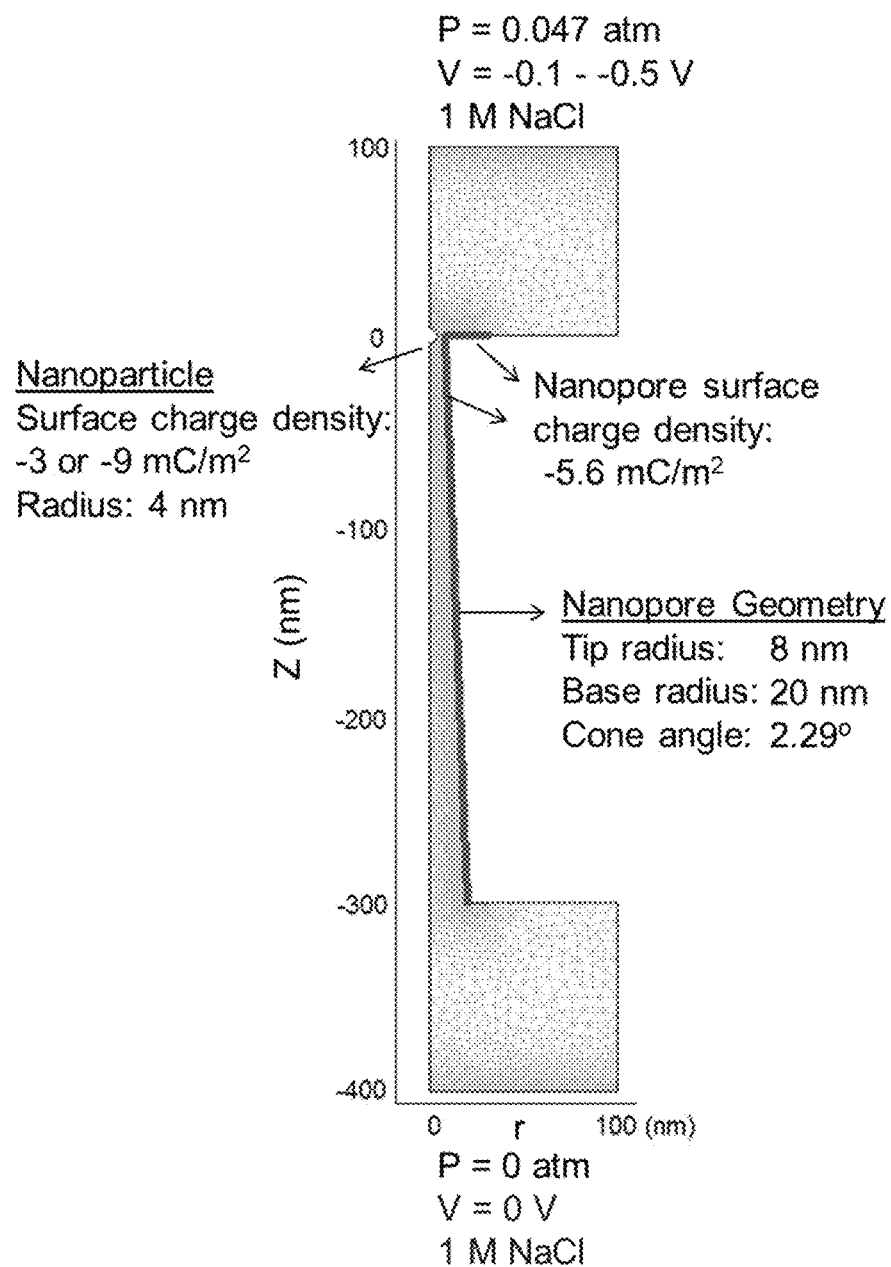
FIG. 12 shows geometry and boundary conditions for the finite-element simulation in 1M NaCl and 0.047 atm.

The same method to determine surface charge and geometry as in the example of FIG. 11, which is based on the ion current rectification ratio, was not employed here, because 1 M NaCl screens the surface charge and almost eliminate the ion rectification. However, we can obtain additional information about the nanopore geometry from the resistive pulse current blockage. The experimental result shows that at 1 M NaCl and 500 mV, the resistive pulse blockage is ~70 nA which is only twice that of the resistive pulse blockage at 0.1 M NaCl and 500 mV applied voltage (see FIGS. 6A and 6B), less than the expected ~10 fold difference. One possible reason is that the nanopore employed at the higher NaCl concentration is slightly larger than the one used in the lower NaCl concentration experiment, leading to a smaller blockage. Also, to achieve a similar reversal velocity profile between 100 and 500 mV as shown in FIGS. 6A and 6B, the surface charge density was varied and finally chosen as −5.6 mC/m². The increase of surface charge density from −4 mC/m² at 0.1M NaCl to −5.6 mC/m² at 1M NaCl is also justified by Grier et al., who found that a higher concentrated salt solution enhanced the dissociation of surface silanol group, leading to a surface charge density increase.[i] FIG. 12 shows the geometry, mesh, and boundary conditions used in the simulation.

Example 13

Systems for Detecting, Manipulating and Characterizing Gas Nanobubbles and Nanoparticles in Solution Certain embodiments provide systems (e.g., apparatus, devices and the like, including computerized, software augmented or driven systems) for detecting, manipulating and characterizing nanobubbles and nanoparticles in solution.

Particular aspects provide a system or device for detecting, manipulating and characterizing nanobubbles and nanoparticles in solution, comprising: a conduit for saline solution configured to be placed in communication with a source of saline solution (e.g., having nanoparticles or nanobubbles); a conical-shaped nanopore (e.g., conical-shaped glass nanopore) having a nanopore diameter, a proximal end, a distal end in communication with the conduit for saline solution, the conical-shaped nanopore having a nanoparticle or nanobubble sensing zone between the proximal and the distal ends, and wherein the sensing zone of the conical-shaped nanopore has a half-cone angle sufficiently small to provide for significant channel-like character at the nanopore; electrodes (e.g., an electrode pair) positioned on opposite sides of the conical-shaped nanopore, the electrodes in communication with a voltage/potential source, and configured to provide for application of a voltage/potential across the nanoparticle or nanobubble sensing zone between the proximal and the distal ends to provide an electrophoretic force (EPF) across the nanopore; a nanopore/electrode holder in communication with a source of pressure, and configured to provide for application of pressure within the conical-shaped nanopore; a current measuring component (e.g., a suitable amplifier) configured to be in operative communication with computer-implemented data acquisition software suitable to analyze and export current-time traces, and optionally, computer-implemented software suitable to determine translocation peak parameters such as peak position, height, and width at half-height as a function of applied voltage; and control means for adjusting at least one parameter selected from EPF, electroosmottic force EOF, and pressure across the nanopore, to provide for fine control of particle or nanobubble translocation velocities across the sensing zone of the nanopore (e.g., by shifting the zero velocity point to an applied voltage/potential to provide for an acceptable signal-to-noise ratio), to provide a method for detecting, manipulating and characterizing nanobubbles and nanoparticles in solution.

Though the geometry of the GNPs used in this study are conical, they have significant channel-like character due to the small cone angle (~2°; e.g., selected from among: 2°±0.1°; 2°±0.2°; 2°±0.3°; 2°±0.4°; 2°±0.5°; 2°±0.6°; 2°±0.7°; 2°±0.8°; 2°±0.9; 2°±1.0°), and, according to particular aspects of the present invention, this is important in achieving the delicate balance of the forces controlling particle dynamics.

Example 14

Resistive Pulse Sensing

Resistive pulse sensing has garnered significant attention over the last decade as a nanoparticle characterization system. Based on the Coulter principle (DeBlois, R. W., et al., *Journal of Colloid and Interface Science* 1977, 61, 323-335; Coulter, W. H., U.S. Pat. No. 2,656,508, Oct. 20, 1953), the technique makes use of transient interruptions of conductance through a nanopore or nanochannel. The amplitude, duration, and frequency of the resistive pulse provide information about the particle size, charge, and concentration, respectively. Hundreds or thousands of particles are typically studied to gather statistics for an entire dispersion. The measurements of the size or charge of an individual particle, however, are generally associated with relatively large errors.

An individual particle translocation is a stochastic process in which the pulse amplitude depends upon the path taken through the pore (Qin, Z., et al., Measurement Science and Technology 2011, 22, 045804; Berge, L. I., et al., Measurement Science and Technology 1990, 1, 471) and also on the angle of rotation for aspherical particles (Qin, Z., et al., Measurement Science and Technology 2011, 22, 045804; Hurley, J., Biophys J. 1970, 10, 74-79). Additionally, the duration or width of the pulse is randomly affected by diffusional motion of the particle. To reduce errors in nanopore-based DNA sequencing, Gershow et al. advocated recapture and trapping of individual molecules, dubbed "molecular ping-pong" to improve accuracy (Gershow, M., et al., Nature Nanotech 2007, 2, 775-779). Reversal of particle direction based upon the translocation signal has been applied to polystyrene particles (Berge, L. I., et al., Review of Scientific Instruments 1989, 60, 2756-2763; Schiel, M., et al., J Phys. Chem. C 2014, 118, 19214-19223), DNA (Gershow, M., et al., Nature Nanotech 2007, 2, 775-779; Sen, Y.-H., et al., Lab on a Chip 2012, 12, 1094), dissolving bubbles (Berge, L. I., et al., Review of Scientific Instruments 1989, 60, 2756-2763; Berge, L. I., Journal of Colloid and Interface Science 1990, 134, 548-562), and microorganisms (Berge, L. I., et al., Review of Scientific Instruments 1989, 60, 2756-2763; Boyd, C., et al., Journal of Plankton Research 1995, 17, 41-58) providing information about particle diffusion, recapture rates (Gershow, M., et al., Nature Nanotech 2007, 2, 775-779; Schiel, M., et al., J. Phys. Chem. C 2014, 118, 19214-19223; Sen, Y.-H., et al., Lab on a Chip 2012, 12, 1094; Lan, W.-J., et al., ACS Nano 2012, 6, 1757-1765), bubble dissolution, viscosity effects, off-axial translocations, and aspherical particle orientation (Berge, L. I., et al., Review of Scientific Instruments 1989, 60, 2756-2763; Berge, L. I., Journal of Colloid and Interface Science 1990, 134, 548-562). Both voltage and pressure switching have been used to reverse particle direction. Although Gershow et al. (Gershow, M., et al., Nature Nanotech 2007, 2, 775-779) raised the possibility, only Sen et al. (Sen, Y.-H. et al., Lab on a Chip 2012, 12, 1094) and Berge et al. (Berge, L. I., et al., Review of Scientific Instruments 1989, 60, 2756-2763) focused on repeated reversals of individual particles for the purpose of increasingly accurate characterization. Sen et al. involved high aspect ratio DNA particles, and Berge, et al., studied various low aspect ratio micro-scale particles. There is a general need for high-resolution characterization of individual nanoparticles in their native solution state. Recent advances position resistive pulse sensing to address this problem.

Conical nanopores have unique advantages over rectangular nanochannels and cylindrical solid-state nanopores due to their ability to control nanoparticle dynamics, measure small particles, and significantly improve the probability that a particle "captured" from one side of the pore will be "released" back to that side by a return translocation (Lan, W.-J., et al., ACS Nano 2012, 6, 1757-1765; German, S. R., et al., J. Phys. Chem. C 2013, 117, 703-711; Kozak, D., et al., ACS Nano 2012, 6, 6990-699; Lan, W., University of Utah, 2012; Luo, L., et al., Annual Review of Analytical Chemistry 2014, 7, 513-535). The present experiments employ a conical nanopore in an automated pressure-reversal system that allows controlled trapping, and repeated translocations, of individual particles based on automated electronic triggering of the particle motion using the translocation pulses. This approach permits multiple observations of single particles, thereby improving measurement resolution to sub-nanometer levels traditionally associated with ex situ electron microscopy. These methods are applied to resolve the radii of individual Au nanoparticles to an unprecedented 0.3 nm size resolution, to detect subtle differences in the surface charge of particles, and to gain a better understanding of the intrinsic variability in resistive pulse sensing.

Example 15

Materials and Methods for Resistive Pulse Technique

Chemicals and Materials: Quasi-spherical Au nanoparticles with radii of 33-nm±4% and 59-nm±4%, both conjugated with a methylated polymer, and 59-nm±4% radius conjugated with a carboxylated polymer were purchased from Nanopartz (Loveland, Colo.). Zeta potentials were measured as −12, −18, and −35 mV, respectively, in deionized water. Other materials included borosilicate glass capillaries (o.d. 1.5 mm, i.d. 0.86 mm, length 10 cm, Sutter Instruments), hydrofluoric acid (48%), ammonium fluoride solution (40%), sodium chloride, monosodium phosphate, disodium phosphate, Triton X-100, 0.25 mm silver wire (World Precision Instruments), 6 µm electroplated diamond on brass sanding disk (Ted Pella), nitrogen, hot glue, and household bleach (5% hypochlorite). Solutions were filtered through Millex-VV 0.1 µm syringe filters (Millipore, Billerica, Mass.).

Glass Nanopore:

Fabrication of nanopores was as previously described (see Example 1 and German, S. R., et al., J. Phys. Chem. C 2013, 117, 703-711), with the following modifications. Sanding of the terminal bulb was carried out above an inverted microscope (Olympus IX50 with an LMPlanFL 20×/0.40 objective) as the capillary was held by a micropositioner and pressed onto a diamond sanding disk (3M 6 micron diamond sanding disc metal bond 6ME5) rotated by a DC motor. The sanding was stopped just before the nanopore was opened, and the capillary was immediately filled with 1.0 M NaCl. For hydrofluoric acid etching, an automated etching system was constructed to hold the capillary on a vertically oriented circular platform with a stepper motor mounted to the shaft. A milled Teflon block with two wells containing electrodes was used to hold minimal amounts of 4:1 48% HF:40% $NH_4F$ and NaCl solutions. An idler gear and second circular platform were positioned directly above the drive-mounted platform to ensure correct orientation of the pipette in the etchant and quenching solutions. The control system consisting of a microcontroller (Arduino Uno R3), highspeed stepper motor, and custom software read the amplified signal from the Princeton Applied Research 2273 PARSTAT potentiostat. Once a jump in the current indicated pore formation, the system immediately moved the capillary out of the etchant and into the quenching solution in under 0.1 seconds. After forming a pore, capillaries were stored in a solution matching that inside the capillary. Pores were widened to the desired radius by etching further in 60:1 buffered hydrofluoric acid while applying a positive pressure of ~5 psi across the pore. Between successive etches, resistive pulse measurements were made using Au nanoparticle standards. At a threshold size where approximately half of the particles pass through the pore and half block the pore entrance, the pore radius can be equated to the particle radius, and calculate the nanopore's half cone angle by $R_p = 1/(\kappa r)[1/4 + 1/(\pi \tan \Theta)]$ (White, H. S.; Bund, A., Ion Current Rectification at Nanopores in Glass Membranes. Langmuir 2008, 24, 2212-2218) where $R_p$ is the resistance of the pore, r is the radius of the pore opening, κ is the solution conductivity, and Θ is the half cone angle. This same cone angle is used in calculating pore radii upon further etching.

Differential Pressure Particle Trapping System:

A purpose built pressure chamber (Automated Systems, Tacoma) allowed electrical and pneumatic connection to a BNC style micropipette holder with a pressure port (QSW-B15P, Warner Instruments). Command signals from a custom LabVIEW program via an AD/DA (USB-6211, National Instruments) were sent to an electrically controlled proportional valve regulator (QPV1, Proportion Air) pressurized by a nitrogen tank. The program reads in voltage values from the resistive pulse amplifier at 10 kHz, calculating the slope of every ~4 data points. Slopes exceeding a pre-defined threshold triggered the differential pressure switch. Detection cycles required less than 1 ms, although 1- to 5-ms delays were inserted to avoid duplicate detection of the same signal. The pressure response of the regulators was the factor limiting the detection cycle.

Resistive Pulse Sensing Measurements and Data Analysis:

i-t traces and differential pressure were recorded using a HEKA EPC-10 USB amplifier at a cutoff frequency of 10 kHz applied with a three-pole Bessel low-pass filter. Patchmaster data acquisition software was used to collect and export raw data. A custom VBA Excel program was used to determine resistive pulse parameters. Each peak was inspected manually to ensure accurate measurements.

Example 16

Controlling Nanoparticle Motion Via Reversal of Applied Pressure

The origin of the forces acting on charged nanoparticles in conical nanopores, namely electrophoretic force (EPF), electroosmotic force (EOF), and forces due to applied pressure, have been described in the preceding examples, and the use of the simultaneous application of external pressure and voltage to precisely control particle velocity has been demonstrated (German, S. R., et al., *J. Phys. Chem. C* 2013, 117, 703-711). This work has been built upon to control the motion of individual particles in driving them back and forth through the orifice of a conical nanopore. FIG. 13A shows a schematic drawing of the basic measurement concept, depicting a nanoparticle drawn from the bulk solution across the nanopore orifice (i.e., the "sensing zone") and then, at a controlled time following the resistive pulse, the velocity of the particle is reversed, thereby driving the particle back into the bulk solution. As demonstrated in the present example and those that follow, the magnitude of the applied pressure is the dominant factor influencing particle motion, as it is kept relatively large compared to the electrokinetic forces (EPF and EOF). Under these conditions, applying a negative pressure pulls a particle into the capillary through the sensing zone, while applying positive pressure releases the particle back out of the capillary. A unique feature of these experiments is that the translocations immediately trigger a reversal in the applied pressure. Rapid pressure reversal upon detection of a particle is important to ensure that the same particle translocates back through and forth through the pore multiple times.

The process of particle reversal within the conical nanopore is illustrated in FIG. 13A for the analysis of a 59-nmnm Au nanoparticle; an EM image of a glass nanopore cross section is shown in FIG. 13B. Although the pore in the TEM image is not the same one used for the present trapping experiments, it was fabricated by the same capillary pull-and-melt process method. Imaging nanopores of this type is a significant challenge due to the difficulty of locating the pore opening (DeBlois, R. W., et al., *Rev Sci Instrum* 1970, 41, 909-916; Gao, C., et al., *Anal. Chem* 2009, 81, 80-86). Importantly, the geometry in the image confirms the −2° cone angle estimated by independent size threshold measurements in German et al. for pores prepared by the same method (German, S. R., et al., *J Phys. Chem. C* 2013, 117, 703-711). (Details regarding the preparation of nanopore lamella for TEM and corresponding images are provided in FIGS. 14A-C.).

FIG. 13C shows the measured current under −300 mV applied potential (black trace) and pressure changes (blue trace), which correspond to the particle motion illustrated in FIG. 13A. The resistive pulse at 5.63 s indicates a particle passing into the pore from the external solution as the result of a differential pressure of −3 psi (lower pressure within the capillary relative to the external solution). The current pulse has an asymmetric shape, decreasing sharply as the particle approaches the pore orifice from the bulk solution and increasing back to the open pore current more slowly as the particle moves up into the conical nanopore. The change in resistance due to particle translocation is detected in real time, and, within ~20 ms of the translocation, the direction of fluid flow is reversed using LabVIEW software and an automated electronic system to increase the pressure to +1 psi within the capillary, causing the particle to reverse direction. The particle then passes through the pore in the opposite direction as indicated by the asymmetric translocation pulse at 5.71 s, which has a shape that is the mirror image of the preceding pulse. The particle translocation continues to trigger pressure reversals resulting in additional translocations (e.g., 5.76 s). The gradual fall and rise of the current baseline with the pressure swings has been noted before (Lan, W. J., et al., *The Journal of Physical Chemistry C* 2011, 115, 18445-18452; Vogel, R., et al., *Anal. Chem* 2012, 84, 3125-3131). These slow baseline oscillations arise from a combination of ion current rectification and slightly different salt concentrations on either side of the pore due to evaporation (on the order of a ~1% difference).

Significantly, the precision in estimating the particle size and other characteristics based on pulse height and width improve as the number of back-and-forth translocation cycles increases. To achieve multiple measurement cycles that allow sub-nanometer size resolution, a system was designed that encloses the capillary-based nanopore within a chamber in which the pressure is held constant by a proportional valve electronic pressure regulator (FIG. 15A). A dual proportional valve electronic differential pressure regulator is referenced to the chamber pressure and allows both positive and negative pressure to be applied within the capillary to within ±0.0008 psi. By monitoring the slope of the current-time (i-t) trace, the reversal of pressure can be triggered from positive to negative, and vice versa, upon detection of a translocation event. Electronic triggering allows multiple resistive pulse measurements on the same nanoparticle. As shown below, typically between 20 and 70 translocation cycles are performed on each particle.

A corresponding system was designed that encloses the capillary-based nanopore within a chamber in which the pressure is held constant by a proportional valve electronic pressure regulator, wherein the differential pressure regulator can hold the pressure constant inside the capillary-based nanopore, wherein the voltage within the capillary-based nanopore can be changed in order to capture/release a nanoparticle or nanobubble through the pore (FIG. 15B).

Example 17

Figure 16A:
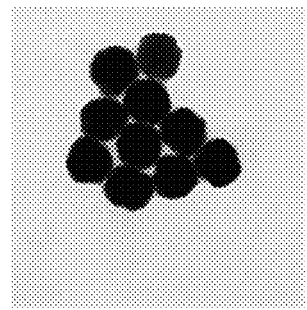
FIGS. 16A, 16B, and 16C show, according to particular exemplary aspects, the particle sizing from TEM images. (A) TEM image of 33-nm radius spherical Au nanoparticles. (B) Radii of particles were determined by analysis with ImageJ software by measuring the area of each particle cross section and calculating the radius from $r=(Area/\pi)^{1/2}$. This calculation assumes a spherical particle for simplicity, although some particles are clearly non-spherical. (C) TEM image of the nominally 59-nm radius particles. The radii of 120 particles were measured, and the distribution of radii was 59±4 nm (1 σ). This mean value served as the calibration reference for correlating resistive pulse heights with absolute particle size.
Figure 16B:
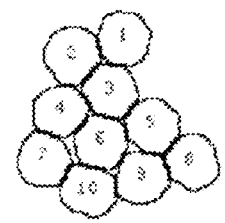
Figure 16C:
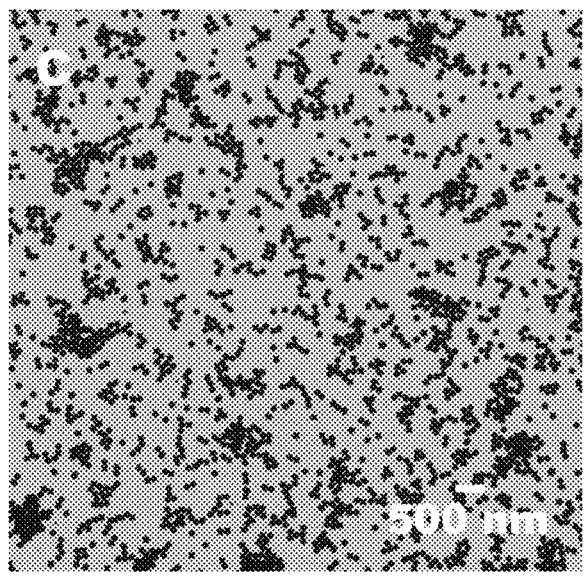

Determination of Nanoparticle Size from Highly Resolved Resistive Pulse Measurements These experiments utilized well-characterized spherical Au nanoparticle system of two different radii. For the larger particle size, two different surface charges were also studied, one with a carboxylated or a methylated polymer coating in order to assess the effect of particle charge. TEM images of the larger radius particles in their dried state were analyzed with ImageJ software (FIG. 16). Based upon images of 120 particles, the particle size distribution was determined to be 59±4 nm (±1σ). Application of standard error of the mean (SEM=σ/√N) gives a 99.7% confidence interval, or ±3 SEM, that the mean radius is 65±2 nm. Resistive pulse sensing does not allow direct absolute measurement of a particle's size at high resolution. Therefore, we calibrated the present nanopore system by assigning the mean radius derived from TEM images to the percent current blockade of the mean particle size resulting from hundreds of resistive pulse measurements on the same particles dispersed in solution. Each different nanopore used needs to be calibrated in this way because of uncertainties in the pore size and geometry. Trapping experiments were performed in numerous pores, but unless specified, the data presented in this paper is derived from experiments using a single ~80 nm radius nanopore. (Details for determining pore radii can be found in the methods section.) Based on measurements of 250 particles in a 1 M NaCl solution with 0.1% Triton X-100 at pH 7.2.

Figure 17:
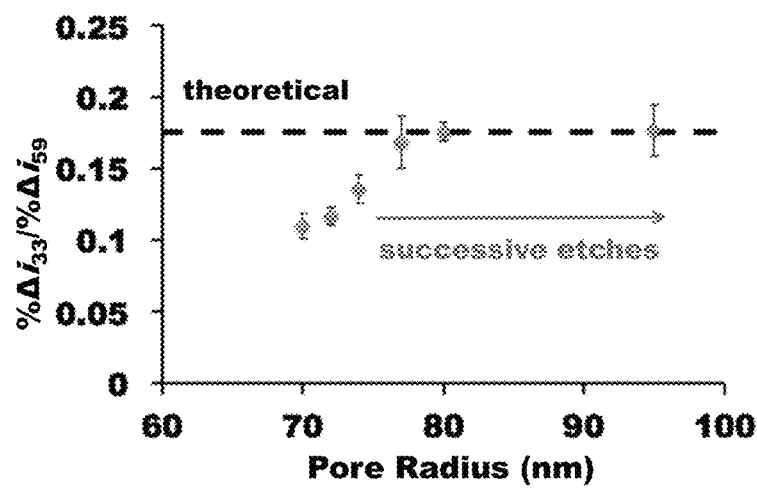
FIG. 17 shows, according to particular exemplary aspects, particle/pore size ratio effects. The ratio of the current blockades for the two particle sizes (33- and 59-nm radius) plotted versus the estimated pore radius. As an individual conical pore is successively etched to wider dimensions, resistive pulse measurements were made using the two particles of different sizes. Once the pore is etched to ~80 nm, the ratio of the average resistive pulse heights for the two particles remained constant indicating that the correction factor described by Deblois and Bean for closely matched particle and pore sizes could be neglected (DeBlois, R. W.; Bean, C. P. Counting and Sizing of Submicron Particles by the Resistive Pulse Technique. *Rev Sci Instrum* 1970, 41, 909-916). The error bars represent 1 SEM.

59-nm radius Au nanoparticles translocating through this pore gave an average percentage blockage current (% Δi) of 4.5%, where Δi is defined as the change in current due to the transient particle blockage relative to the baseline current. Since the resistive pulse height is proportional to the volume of electrolyte excluded by the translocating particle (Lan, W.-J. et al., *Anal. Chem* 2011, 83, 3840-3847):

$$\% \Delta i = k r_p^3 \quad (1)$$

where k is a proportionality constant relating % Δi, to the nanoparticle radius, $r_p$. The value of k determined using the 59-nm radius Au nanoparticles, k=4.5%/(59 nm)³ (Rasteiro, M. G., et al., *Particul Sci Technol* 2008, 26, 413-437), was then used to measure the radius of a second nanoparticle of different size based upon its resistive pulse height (using the same pore). The direct relation of particle volumes to resistive pulse heights has been shown to hold within ~2% as long as the particle/pore diameter ratio is below 0.8.[23] To confirm measurements took place in this linear regime, the pores used for this work were etched successively wider (in dilute, buffered hydrofluoric acid while under an applied pressure of 5 psi as described in German, et al., *J. Phys. Chem. C* 2013, 117, 703-711), and additional resistive pulse traces were collected between etches for two particles of different radii (33- and 59-nm). The ratio of resistive pulse heights for the two particle sizes reaches a constant value for pores greater than 80 nm (FIG. 17), justifying the use of equation 1.

% Δi values can be readily determined to with 0.1% (vide infra) by measuring the resistive pulse height for repeated translocations of the same nanoparticle, allowing its radius to be determined with a precision of less than 1 nm. Of course, the absolute accuracy in determining the particle size depends on the calibration of the resistive pulse magnitudes using the TEM-measured value of the average radius as the calibration standard, which in this case is ~2 nm based on TEM images of the 59-nm Au particles.

Figure 18A:
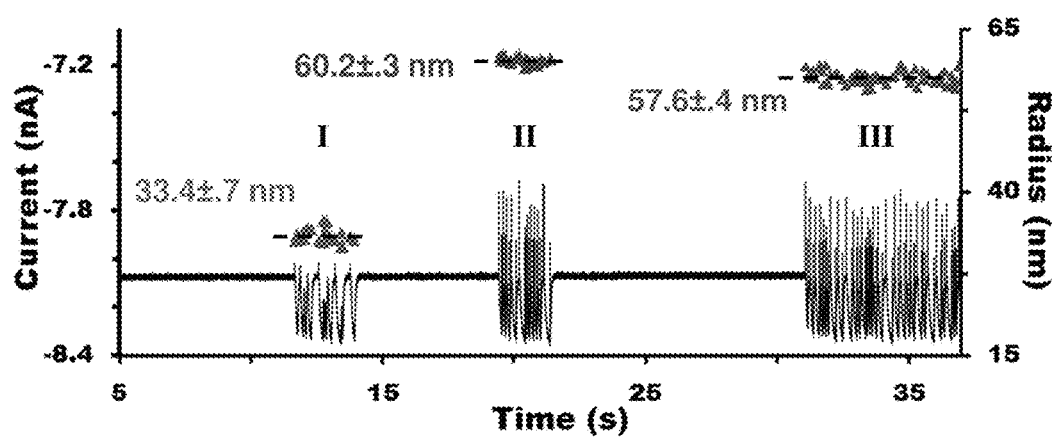
FIGS. 18A and 18B show, according to particular exemplary aspects, trapping and analysis of particle size in solution containing both 33-nm and 59-nm radius Au nanoparticles. (A) A section of an i-t trace current showing relatively long periods of open pore current, interdispersed by three particle trapping and size-measurement cycles. (B) Expanded i-t trace from each trapping event in (A) showing two sets of forward and reverse translocations. The current baseline falls and rises with the pressure swings as described in the text. Measurements were made in a 1 M NaCl pH 7.2 solution containing 0.1% Triton X-100, using a nanopore with an ~80 nm radius orifice. The particle radius calculated by a volumetric relationship from the resisitve pulse heights is shown as individual points in (A); the dashed line and numerical value correspond to the average radius calculated for each particle. 99.7% confidence intervals are provided in each case, representing 3 times the standard error of the mean based on 24, 21, and 62 size-measurement cycles of the three particles, respectively.
Figure 18B:
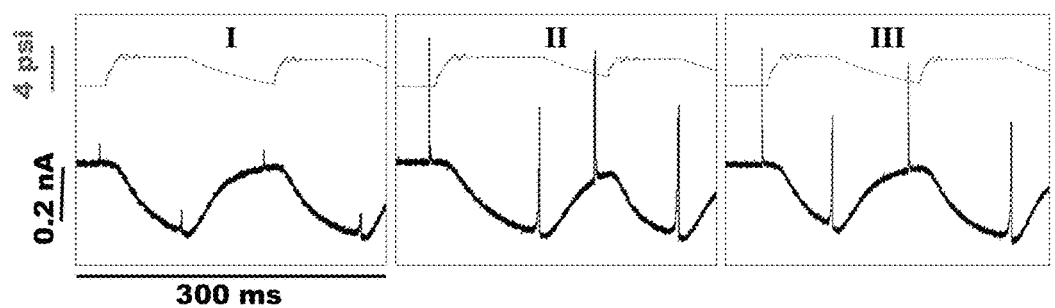

The second Au particle size used in this study had a nominal radius of 33 nm, as determined by TEM (FIG. 16). Resistive pulse sensing of a solution containing these nanoparticles yielded an average percent current blockade ~⅙ as large as that of the 59-nm particles, consistent with the predicted value of 0.17 (~⅙) based on equation 1. FIG. 18A shows the i-t trace for a resistive pulse measurement performed in a solution containing both 59- and 33-nm radius Au nanoparticles; in this representative trace, three individual Au nanoparticles were trapped and their radii measured over a time period of 25 s. Because the particle concentration is fairly low ($10^9$ particles/mL), there are relatively long stretches of time during which the open-pore current is measured while applying a negative pressure inside the nanopore. However, once a particle enters the pore, it ping pongs back and forth through the sensing zone at a frequency of ~10 $s^{-1}$ until it is manually ejected or is lost due to recapture failure, as discussed below. For the i-t trace shown in FIG. 18A, the first, second, and third particle made 24, 21, and 62 cycles, respectively, of passing back and forth through the sensing zone. The study of each of these specific particles was terminated when the particle diffused away from the pore. While the i-t trace in FIG. 18A appears complex, the expanded view of the i-t trace for each particle, shown in FIG. 18B, shows well resolved forward and reverse translocations.

The particle radii calculated from each translocation event using equation 1 are plotted directly above each corresponding peak in FIG. 18A, along with the group mean. Each grouping of events can unequivocally be distinguished from another grouping as representing a new particle with a different mean radius. Repeated measurement of the resistive pulse peak height allowed the radii to be calculated as 33.4±0.7 nm, 60.2±0.3 nm, and 57.6±0.4 nm (3 SEM based upon 24, 21, and 62 measurements, respectively).

Figure 19:
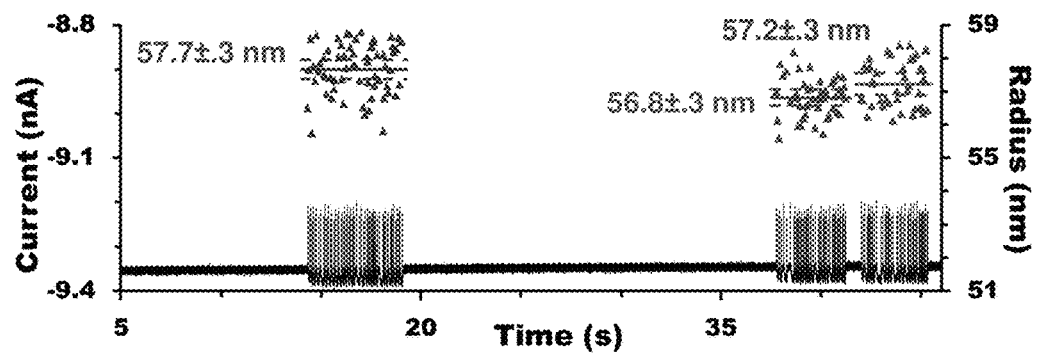
FIG. 19 shows the trapping and analysis of particle sizes in solution containing 59-nm radius carboxylated Au particles. Section of an i-t trace showing periods of open pore current interdispersed by three particle trapping and size measurement cycles. The radii calculated from the % current blockade is plotted above each translocation event. Each solid line represents the mean size, and the dashed line represents 3 standard errors from the mean (3 SEM based upon 62, 47, and 43 measurements). Measurements were made in a 1 M NaCl, pH 7.2 solution containing 0.1% Triton X-100 using a ~95 nm radius pore calibrated using equation (1) where $k=1.7\%/(59\text{ nm})^3$.

FIG. 19 demonstrates the unprecedented size resolution afforded by the resistive pulse technique. In this 30 s trace, three particles that differ in absolute size by less than 1 nm are sequentially captured, and each undergoes 40-60 translocation reversals. Statistical averaging of the pulse heights allow their radii to be determined as 57.7±0.3, 56.8±0.3, and 57.2±0.3 nm (3 SEM based upon 62, 47, 43 measurements).

The end of a trapping sequence on a single particle can be caused by a number of circumstances other than diffusion of the particle away. Despite the particle concentration being kept low, a second particle can occasionally enter the pore, doubly triggering the pressure system such that the pressure does not reverse. Also, a particle that passes through the pore when the differential pressure is less than 0.1 psi can have a peak width at half maximum several milliseconds long in which case the rate of change in current is not large enough to trigger a reversal. This is particularly an issue when triggering on small resistive pulse amplitudes, because the slope detection system will false trigger on the baseline oscillations if the threshold is set too low. If a trapping sequence is successful in acquiring sufficient data for the needs of the study, researcher intervention may also terminate the experiment. In this study, a particle was lost due to diffusion, researcher intervention, trigger failure, or a second particle approximately 50%, 33%, 12%, and 5% of the time, respectively, based on capture and analysis of ~300 different nanoparticle.

Example 18

Effects of Asphericity on Nanoparticle Size Measurements

The resistive pulse technique is generally described as a single particle technique. However, the source and magnitude of variability in measuring particle size based on individual translocation events is often neglected in analyses due to the difficulty in repeating the measurement on the exact same particle.

The distribution of resistive pulse amplitudes for a single particle represents a combination of complex stochastic phenomena. First, the nanoparticle translocates through the nanopore orifice at different radial distances from the pore axis, which has been theoretically shown to produce different blockage currents (Qin, Z., et al., *Measurement Science and Technology* 2011, 22, 045804).

Figure 20A:
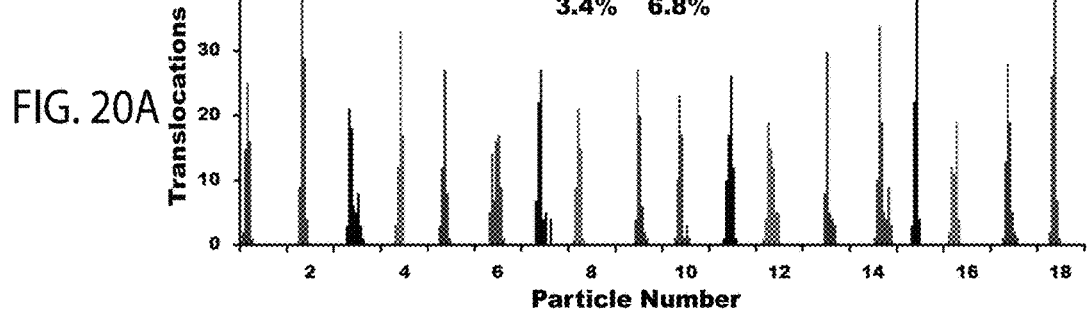
FIGS. 20A and 20B show, according to particular exemplary aspects, histograms of the percentage current blockade in which 59-nm radius particles were trapped and between 45-70 translocation cycles were recorded for each particle. Representative histograms for 18 different nanoparticles are shown, binned at 0.2% intervals to make the line widths visible. The intervals along the x axis correspond to a range of percentage current blockades between 3.4 and 6.8% for each individual particle. (B) Expanded view of the distributions for 3 different particles binned at 0.1% intervals (corresponding to particles 1, 2, and 3 in part (A)). The blue and red lines are gaussian distribution fits; the black line is drawn to guide the eye. The distribution widths represent contributions from off-axial translocation and particle asphericity.
Figure 20B:
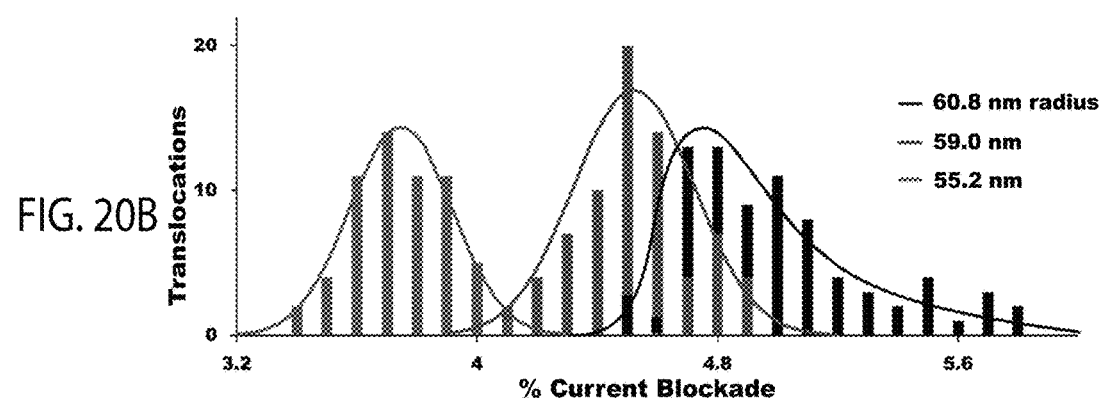

A 15% maximum spread in $\Delta i$ is predicted for off-axial translocations of perfectly spherical nanoparticles. Second, numerical modeling also shows that the orientation of aspherical particles significantly influences the peak amplitude (Qin, Z., et al., *Measurement Science and Technology* 2011, 22, 045804; Hurley, J. *Biophys J.* 1970, 10, 74-79; Golibersuch, D. C., et al., *Biophysical Journal* 1973, 13, 265-280). The Au nanoparticles used in the present experiments are nominally spherical, but it is apparent from the TEM images (FIG. 16) that some are slightly oblong. In one experiment, % $\Delta i$ histograms were collected for ~200 individual ~59-nm radius particles, of which 18 representative examples are shown in FIG. 20A. FIG. 20B shows expanded views of % Ai distributions for three different particles. Clearly, two of the distributions are nearly symmetrical, while the third is markedly skewed. Approximately ⅓ of the particles trapped and analyzed exhibit a skewed distribution, and the widths of the distributions were significantly larger (25-40%) than the 15% maximum predicted for off-axial translocations of perfect spheres (Qin, Z., et al., *Measurement Science and Technology* 2011, 22, 045804). The 25-40% spread in $\Delta i$ values can provide information about particle asphericity, with the smaller $\Delta i$ values representing the particle's major axis aligned with the pore axis and the larger $\Delta i$ values resulting as the particle's major axis and radial position departs from the pore axis (Qin, Z., et al., *Measurement Science and Technology* 2011, 22, 045804; Golibersuch, D. C., *Biophysical Journal* 1973, 13, 265-280).

Example 19

Determination of Nanoparticle Size Dispersion

Figure 21:
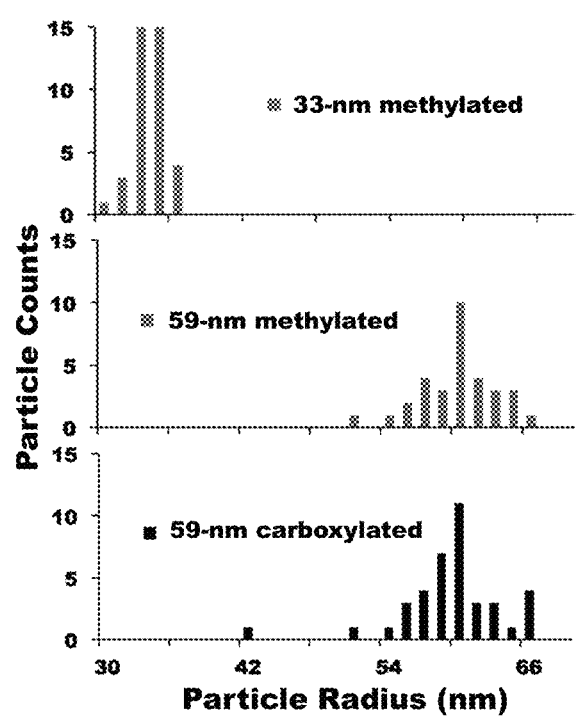
FIG. 21 shows histograms of the radii of ~40 particles from each particle type. Each count represents the mean radius determined from 20-70 translocation cycles of an individual particle. Particle sizes were measured in 1 M NaCl and 0.1% Triton X-100, pH 7.2 using an ~80 nm radius pore.

By measuring the radii of many individual nanoparticles, the size dispersion of a collection of particles can also be determined FIG. 21 shows the size histograms of the 33-nm radius methylated, 59-nm radius methylated and 59-nm radius carboxylated Au nanoparticles, based on individual particle size measurements, each with sub-nanometer resolution. The automated trapping and multiple translocation methodology presently described can therefore provide particle size distribution profiles at a resolution that has been hitherto unattainable in solution. Note that the widths of the size distributions (~5 nm for the 33-nm radius Au nanoparticles, and ~10 nm for the 59-nm radius Au nanoparticles) are much larger than the 0.3-0.7 nm precision in measuring individual particle sizes. Thus, because the variability in single particle radii is significantly less than the ensemble distribution widths, the distributions shown in FIG. 21 reflect the true distribution of particle sizes.

Example 20

Effects of Salt Concentration and Particle Charge on Nanoparticle Dynamics and Size Measurements It has been previously demonstrated that the particle velocity increases linearly with increasing pressure (Li, G.-X., et al., *Chinese Journal of Analytical Chemistry* 2010, 38, 1698-1702). The effect of electrical charge on a particle's velocity during translocation is also well understood (DeBlois, R. W., et al., *Journal of Colloid and Interface Science* 1977, 61, 323-335; German, S. R. et al., *J. Phys. Chem. C* 2013, 117, 703-711; Kozak, D. et al., *ACS Nano* 2012, 6, 6990-6997; Ito, T. et al., *Anal. Chem* 2003, 75, 2399-2406). The duration of the resistive pulse (measured by the peak width at half-height) is governed by both the velocity of pressure driven flow as well as electrokinetic phenomena associated with the charged particle and nanopore. The electrokinetic forces are typically simplified as electrophoretic (EP) forces on the particle and electroosmotic flow (EO) within the pore. EO manifests as a plug flow of fluid arising from the counterions associated with the charged walls, whereas, the EP is dependent upon the charge of the particle (Li, G.-X. et al., *Chinese Journal of Analytical Chemistry* 2010, 38, 1698-1702). In the present experiments, the glass nanopore has a negative surface charge, and, therefore, the net excess of positive counterions in the electrical double layer, under the influence of negative potentials, drag fluid into the pore by EO toward the cathode. Both the methylated and the carboxylated Au nanoparticles used in the present experiments are negatively charged (DLS measured zeta potentials in deionized water yield-12 mV and −18 mV for the 33- and 59-nm radius methylated particles, and −35 mV for the 59-nm carboxylated particles, respectively) and, thus, are subjected to a repulsive force directed out of the pore at negative applied potentials; the more highly charged carboxylated particles experience a larger EP force directed out of the pore.

Figure 22A:
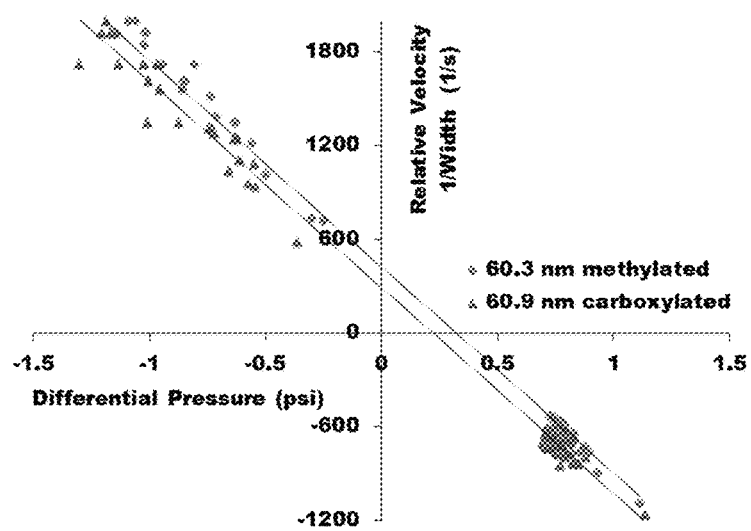
FIGS. 22A and 22B show, according to particular exemplary aspects, relative nanoparticle translocation velocity vs differential pressure during a trapping sequence under −300 mV applied potential (pressure and voltage are external vs internal solution). (A) Data for a single 60.3±0.4 nm methylated particle (blue diamonds) and an individual 60.9±0.3 nm carboxylated Au particle (red triangles). Particles enter the pore under negative pressures and exit the pore under positive pressures. The y-intercept of the fitted line represents the particle velocity at zero applied pressure, and corresponds to the relative electrokinetic velocity. (B) Plot of relative electrokinetic velocities at −300 mV as a function of particle radius for individual particles in 0.2 and 1.0 M NaCl solutions demonstrating simultaneous determination of particle size and relative charge.

A particle's relative velocity through the nanopore due to the above forces is obtained from the duration of the resistive pulse, the latter measured as the reciprocal peak width at half maximum. FIG. 22A plots the relative velocity of an individual 60.3±0.4 nm methylated and a 60.9±0.3 nm carboxylated particle as a function of the differential pressure across the nanopore, while holding the applied voltage constant at −300 mV. Each set of data comes from trapping and repeated translocation of one particle at different pressures (34 and 42 measurements for the methylated and carboxylated particles, respectively) The tight grouping of reciprocal peak widthsat positive pressures is a result of the differential regulator achieving its setpoint value quickly as the pressure is increased, causing each translocation exiting the pore to occur at nearly the same velocity. In the present system, decreasing the differential pressure requires a longer time, and, thus, the negative differential pressure value at which the particle returns into the pore has a greater variability, a consequence of the random diffusion of the particles. FIG. 22A clearly illustrates that the velocity of the nanoparticle passing through the pore orifice is proportional to the instantaneous differential pressure across the orifice at the moment of translocation. FIG. 22A also shows that the additional electrophoretic force on the more highly charged carboxylated particle (red) results in a slight downward shift of the relative velocity versus pressure relationship. Because the applied potential is negative, the more highly negatively charged (red) particle exits the pore more quickly and enters the pore more slowly.

The y-intercepts of the linear fits to the data in FIG. 22A, where the applied pressure is zero, reflects the relative velocity of the two particles resulting solely from electrokinetic forces. Both particles have a positive velocity (into the pore) in the absence of applied pressure because EO (directed into the pore) is the stronger electrokinetic force; however, the electrokinetic velocity is ~25% slower for the more highly charged carboxylated particle due to stronger EP (directed out of the pore). (Zeta potential measurements could not be performed in higher NaCl concentrations, but the values would be expected to be much lower.)

Figure 22B:
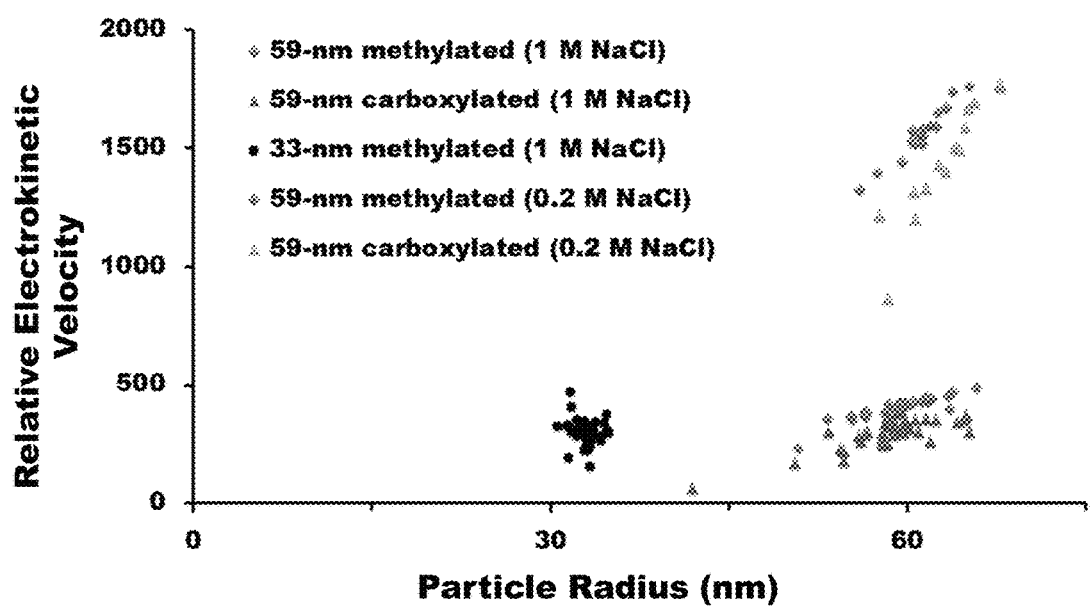
Figure 23:
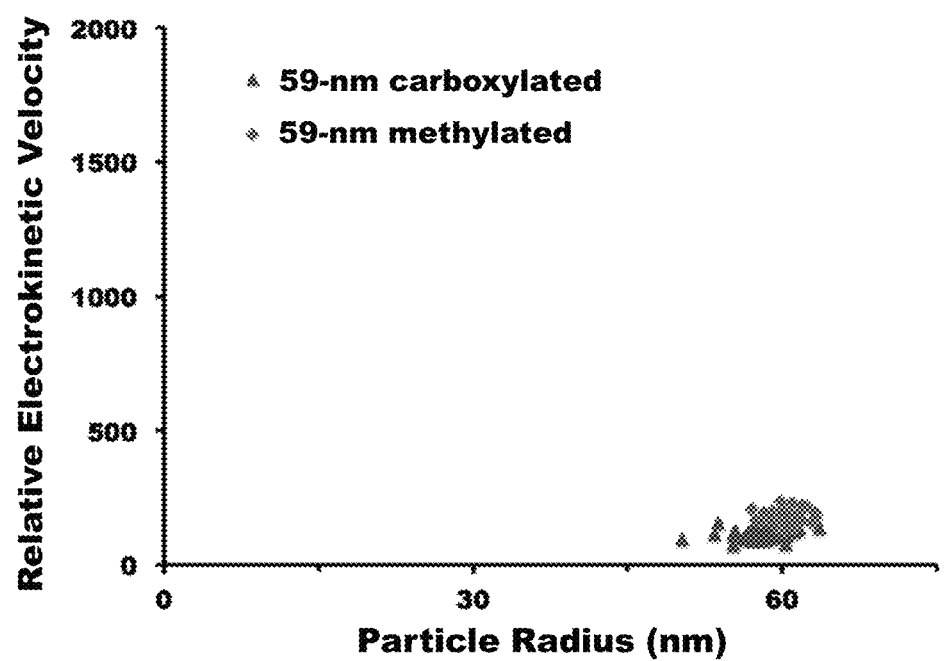
FIG. 23 shows a plot of the relative electrokinetic velocity (extracted from the y-intercepts of plots of relative velocity vs differential pressure, analogous to that shown in FIG. 22A) versus particle radius for nominally 59-nm radius particles. These experiments were performed using a ~59-nm radius pore. Notably, the dependence of electrokinetic velocity on the particle radius observed with the smaller ~80-nm radius nanopore (see FIG. 22B) is no longer present. This finding supports the proposal that the influence of electroosmosis on particle velocity is significantly influenced by the size of the gap between the particle and pore wall. For the 59-nm radius particles, the size of the gap using this ~95-nm pore is ~67% larger compared to the gap width for the same particles translocating through the ~80 nm pore in FIG. 22B. As a result, the field strength in the gap would be expected to be smaller, explaining why the dependence of particle velocity on particle radius is no longer observed.

It has been demonstrated previously with resistive pulse sensing that both the size and charge of individual particles can be measured simultaneously (DeBlois, R. W., et al., *Journal of Colloid and Interface Science* 1977, 61, 323-335; Kozak, D., et al., *ACS Nano* 2012, 6, 6990-6997; Ito, T., et al, *Anal. Chem* 2003, 75, 2399-2406). FIG. 22B presents size and relative electrokinetic velocity data collected with the particle trapping system. The results in FIG. 22B were collected using the same nanopore (~80 nm radius) in both 1.0 M NaCl and in 0.2 M NaCl for 33-nm methylated, 59-nm methylated, and 59-nm radius carboxylated spherical Au nanoparticles. Each data point represents a single particle that underwent between 20 and 70 translocation cycles to determine its mean radius and electrokinetic velocity (from the y-intercept of relative velocity vs differential pressure, as in FIG. 22A for two particles). The data in FIG. 22B suggest that the translocation velocity increases with particle size. This observation for the 59-nm radius particle can be attributed to increased EO flow as the gap between the particle and the pore wall gets smaller. The trend of increasing translation velocity with particle size is not apparent for the smaller 33-nm radius particles. Also, lowering the electrolyte concentration to 0.2 M increases the EO significantly, and the trend with particle size becomes more pronounced. The trend disappears in a larger pore (~95 nm radius) while still differentiating the charges of the two particles (FIG. 23).

Example 21

Use of Conical Nanopores Improves Particle Recapture Probability

Manual control of applied pressure has also been used to recapture particles. Using conical glass nanopores, Lan et al. found that the probability of releasing a particle after translocation into the pore was >90% even with delays of 10 seconds before pressure reversal (Lan, W.-J., et al., *ACS Nano* 2012, 6, 1757-1765). However, there is a significant difference in recapture probability for a particle that is confined inside the pore in comparison with a particle that is outside the pore. The fluid velocity falls off radially away from the pore opening, and there is a characteristic distance away from the pore where the diffusional loss of the particle is much more probable than the fluidic velocity pulling the particle back to the pore. However, marked success has been experienced by the present authors using pressure to control the motion. Particle recapture probability is governed by the response time of the system and by the magnitude of the forces applied toward retrieving the particle. Increasing the magnitude of the negative pressure serves to increase the characteristic distance but can also have the detrimental effect of pushing the particle so quickly to the other side of the pore that the automated detection system may not have sufficient time to respond. Conical nanopores ameliorate this issue since recapture becomes almost certain while the particle is inside the pore. Hence, a small positive pressure can be used to retrieve the particle, which carries the particle a shorter distance away from the pore during the system response time after translocation out of the pore. This also allows the application of a large negative pressure for retrieving the particle outside the pore, thereby extending the characteristic recapture distance without any consequence of pushing the particle too far away after recapture into the port. However, there is an upper bound on the range of pressures suitable for the technique, beyond which amplifier bandwidth limitations begin to underestimate peak heights due to excessive particle speeds (Lan, W. J., et al., *The Journal of Physical Chemistry C* 2011, 115, 18445-18452).

The single particle trapping and size measurement system based on differential pressure reversal upon particle detection, as described herein, represents a significant progression in resistive pulse sensing as a single particle characterization method. In addition to providing unprecedented sub-nanometer precision in particle size measurements, repeated measurements of resistive pulses will allow experimental testing of theoretical considerations of the variability inherent to the method. The ability to trap and repeatedly characterize a single particle over a significant length of time also allows for the measurement of the kinetics of subtle surface chemical reactions that result in a change in the size and/or electrical charge of a particle.

Example 22

Systems for Detecting, Manipulating and Characterizing Gas Nanobubbles and Nanoparticles in Solution Based on Changing Voltage within Nanopore Certain embodiments provide systems (e.g., apparatus, devices and the like, including computerized, software augmented or driven systems) for detecting, manipulating and characterizing nanobubbles and nanoparticles in solution based on proximal and distal translocations by means of reversing the voltage across the sensing zone within a nanopore. Preferably this comprises use of suitable computer-implemented data acquisition hardware and software for exporting and analyzing current-time traces of multiple resistive pulses, and further comprise a data acquisition (DAQ) card and/or a field-programmable gate array (FPGA) card.

In preferred aspects, current-time recordings are and were made using a Heka EPC10 USB amplifier connected to a National Instruments USB-7845R field programmable gate array (FPGA) card via analog channels. The FPGA module was programmed to calculate the derivative of the current which in turn triggers voltage switching when the signal from the amplifier exceeds a user-defined threshold. To avoid false triggers, user controllable wait periods can also be adjusted. When configured appropriately for the experimental signal to noise, the voltage will automatically switch polarities after each particle translocation. Data was transferred from the FPGA card to a LabVIEW™ program allowing for real-time updating of the settings to optimize the voltage switching protocol.

INCORPORATION BY REFERENCE

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Accordingly, the invention is not limited except as by the appended claims.

REFERENCES

Incorporated by Reference Herein in their Respective Entireties

1. Domingos, R.; Baalousha, M.; Ju-Nam, Y.; Reid, M.; Tufenkji, N.; Lead, J.; Leppard, G.; Wilkinson, K. Characterizing Manufactured Nanoparticles in the Environment: Multimethod Determination of Particle Sizes. *Environ. Sci. Technol* 2009, 43, 7277.
2. Murray, R. W. Nanoelectrochemistry: Metal Nanoparticles, Nanoelectrodes, and Nanopores. *Chem. Rev* 2008, 108, 2688-2720.
3. DeBlois, R. W.; Bean, C. P.; Wesley, R. K. A. Electrokinetic Measurements with Submicron Particles and Pores by the Resistive Pulse Technique. *Journal of Colloid and Interface Science* 1977, 61, 323-335.
4. Lan, W.-J.; Holden, D. A.; Zhang, B.; White, H. S. Nanoparticle Transport in Conical-Shaped Nanopores. *Anal. Chem* 2011, 83, 3840-3847.
5. Nanotechnology, U. S. N. U.S. National Nanotechnology Initiative (accessed May 30, 2012).
6. Wu, H.-C.; Astier, Y.; Maglia, G.; Mikhailova, E.; Bayley, H. Protein Nanopores with Covalently Attached Molecular Adapters. *J. Am. Chem. Soc* 2007, 129, 16142-16148.
7. Wanunu, M.; Sutin, J.; Ben McNally; Chow, A.; Meller, A. DNA Translocation Governed by Interactions with Solid-State Nanopores. *Biophysical Journal* 2008, 95, 4716-4725.
8. Fologea, D.; Uplinger, J.; Thomas, B.; McNabb, D. S.; Li, J. Slowing DNA Translocation in a Solid-State Nanopore. *Nano Letters* 2005, 5, 1734-1737.
9. Gershow, M.; Golovchenko, J. A. Recapturing and Trapping Single Molecules with a Solid-State Nanopore. *Nature Nanotech* 2007, 2, 775-779.
10. Firnkes, M.; Pedone, D.; Knezevic, J.; Döblinger, M.; Rant, U. Electrically Facilitated Translocations of Proteins Through Silicon Nitride Nanopores: Conjoint and Competitive Action of Diffusion, Electrophoresis, and Electroosmosis. *Nano Letters* 2010, 10, 2162-2167.
11. Zhang, B.; Wood, M.; Lee, H. A Silica Nanochannel and Its Applications in Sensing and Molecular Transport. *Anal. Chem* 2009, 81, 5541-5548.
12. Vogel, R.; Anderson, W.; Eldridge, J.; Glossop, B.; Willmott, G. A Variable Pressure Method for Characterizing Nanoparticle Surface Charge Using Pore Sensors. *Anal. Chem* 2012, 84, 3125-3131.
13. Gao, C.; Ding, S.; Tan, Q.; Gu, L.-Q. Method of Creating a Nanopore-Terminated Probe for Single-Molecule Enantiomer Discrimination. *Anal. Chem* 2009, 81, 80-86.
14. Li, G.-X.; Zhang, Z.-X.; Lin, X.-Q. Fabrication of Glass Nanopore Electrodes for Single-Molecule Detection of Beta-Cyclodextrin. *Chinese Journal of Analytical Chemistry* 2010, 38, 1698-1702.
15. Stöckle, R.; Fokas, C.; Deckert, V.; Zenobi, R. High-Quality Near-Field Optical Probes by Tube Etching. *Appl. Phys. Lett.* 1999.
16. White, H. S.; Bund, A. Ion Current Rectification at Nanopores in Glass Membranes. *Langmuir* 2008, 24, 2212-2218.

17. Vercoutere, W.; Winters-Hilt, S.; Olsen, H.; Deamer, D.; Haussler, D.; Akeson, M. Rapid Discrimination Among Individual DNA Hairpin Molecules at Single-Nucleotide Resolution Using an Ion Channel. *Nature Biotechnology* 2001, 19, 248-252.
18. Lan, W.-J.; White, H. S. Diffusional Motion of a Particle Translocating Through a Nanopore. *ACS Nano* 2012, 6, 1757-1765.
19. Takamura, Y.; Onoda, H.; Inokuchi, H.; Adachi, S.; Oki, A.; Horiike, Y. Low-Voltage Electroosmosis Pump for Stand-Alone Microfluidics Devices. *Electrophoresis* 2003, 24, 185-192.
20. Kozak, D.; Anderson, W.; Vogel, R.; Trau, M. Advances in Resistive Pulse Sensors: Devices Bridging the Void Between Molecular and Microscopic Detection. *Nano Today* 2011, 6, 531-545.
21. Lan, W. J.; Holden, D. A.; Liu, J.; White, H. S. Pressure-Driven Nanoparticle Transport Across Glass Membranes Containing a Conical-Shaped Nanopore. *The Journal of Physical Chemistry C* 2011, 115, 18445-18452.
22. Behrens. S. H. Grier, D. G. The charge of glass and silica surface. *J. Chem. Phys.* 2001, 115, 6716-6721.
23. Browning, N. D.; Bonds, M. A.; Campbell, G. H.; Evans, J. E.; LaGrange, T.; Jungjohann, K. L.; Masiel, D. J.; McKeown, J.; Mehraeen, S.; Reed, B. W.; et al. Current Opinion in Solid State and Materials Science. *Current Opinion in Solid State & Materials Science* 2012, 16, 23-30.
24. Filipe, V.; Hawe, A.; Jiskoot, W. Critical Evaluation of Nanoparticle Tracking Analysis (NTA) by NanoSight for the Measurement of Nanoparticles and Protein Aggregates. *Pharm Res* 2010, 27, 796-810.
25. Coulter, W. H. Means for Counting Particles Suspended in a Fluid. U.S. Pat. No. 2,656,508, Oct. 20, 1953.
26. Qin, Z.; Zhe, J.; Wang, G. Effects of Particle's Off-Axis Position, Shape, Orientation and Entry Position on Resistance Changes of Micro Coulter Counting Devices. *Measurement Science and Technology* 2011, 22, 045804.
27. Berge, L. I.; Jøssang, T.; Feder, J. Off-Axis Response for Particles Passing Through Long Apertures in Coulter-Type Counters. *Measurement Science and Technology* 1990, 1, 471.
28. Hurley, J. Sizing Particles with a Coulter Counter. *Biophys J.* 1970, 10, 74-79
29. Berge, L. I.; Feder, J.; Jøssang, T. A Novel Method to Study Single-Particle Dynamics by the Resistive Pulse Technique. *Review of Scientific Instruments* 1989, 60, 2756-2763.
30. Schiel, M.; Siwy, Z. S. Diffusion and Trapping of Single Particles in Pores with Combined Pressure and Dynamic Voltage. *J. Phys. Chem. C* 2014, 118, 19214-19223.
31. Sen, Y.-H.; Jain, T.; Aguilar, C. A.; Karnik, R. Enhanced Discrimination of DNA Molecules in Nanofluidic Channels Through Multiple Measurements. *Lab on a Chip* 2012, 12, 1094.
32. Berge, L. I. Dissolution of Air Bubbles by the Resistive Pulse and the Pressure Reversal Technique. *Journal of Colloid and Interface Science* 1990, 134, 548-562.
33. Boyd, C.; Johnson, G. Precision of Size Determination of Resistive Electronic Particle Counters. *Journal of Plankton Research* 1995, 17, 41-58.
34. German, S. R.; Luo, L.; White, H. S.; Mega, T. L. Controlling Nanoparticle Dynamics in Conical Nanopores. *J. Phys. Chem. C* 2013, 117, 703-711.
35. Kozak, D.; Anderson, W.; Vogel, R.; Chen, S.; Antaw, F.; Trau, M. Simultaneous Size and Z-Potential Measurements of Individual Nanoparticles in Dispersion Using Size-Tunable Pore Sensors. *ACS Nano* 2012, 6, 6990-6997.
36. Lan, W. Particle Transport and Ion Current Rectification in Conical-Shaped Nanopores, University of Utah, 2012.
37. Luo, L; German, S.; Lan, W.; Holden, D.; Mega, T.; White, H. Resistive-Pulse Analysis of Nanoparticles. *Annual Review of Analytical Chemistry* 2014, 7, 513-535.
38. Lan, W.-J.; Holden, D. A.; White, H. S. Pressure-Dependent Ion Current Rectification in Conical-Shaped Glass Nanopores. *J. Am. Chem. Soc* 2011, 133, 13300-13303.
39. Qin, Z.; Zhe, J.; Wang, G.-X. Effects of Particle's Off-Axis Position, Shape, Orientation and Entry Position on Resistance Changes of Micro Coulter Counting Devices. *Measurement Science and Technology* 2011, 22, 045804.
40. Hurley, J. Sizing Particleswith a Coulter Counter. *Biophysical Journal* 1970, 10, 74-79.
41. Golibersuch, D. C. Observation of Aspherical Particle Rotation in Poiseuille Flowvia the Resistance Pulse Technique. *Biophysical Journal* 1973, 13, 265-280.
42. Ito, T.; Sun, L.; Crooks, R. M. Simultaneous Determination of the Size and Surface Charge of Individual Nanoparticles Using a Carbon Nanotube-Based Coulter Counter. *Anal. Chem* 2003, 75, 2399-2406.
43. German, S. R.; Luo, L.; White, H. S.; Mega, T. L. Controlling Nanoparticle Dynamics in Conical Nanopores. *J. Phys. Chem. C* 2013, 117, 703-711.
44. Schoch, R.; Han, J.; Renaud, P. Transport Phenomena in Nanofluidics. *Rev. Mod. Phys.* 2008, 80, 839-883.
45. Rasteiro, M. G.; Lemos, C. C.; Vasquez, A. Nanoparticle Characterization by PCS: the Analysis of Bimodal Distributions. *Particul Sci Technol* 2008, 26, 413-437.
46. Ruf, H. Treatment of Contributions of Dust to Dynamic Light Scattering Data. *Langmuir* 2002, 18, 3804-3814.
47. Madani, H.; Kaler, E. W. Measurement of Polydisperse Colloidal Suspensions with Quasielastic Light Scattering. *Part Part Syst Char* 1991, 8, 259-266.
48. DeBlois, R. W.; Bean, C. P. Counting and Sizing of Submicron Particles by the Resistive Pulse Technique. *Rev Sci Instrum* 1970, 41, 909-916.

The invention claimed is:

1. A method for determining the size and/or shape of nanobubbles and nanoparticles in solution, comprising:
    (a) placing a conical-shaped nanopore in fluid communication with a fluid having nanoparticles or nanobubbles, the conical nanopore having a half-cone angle, a nanopore diameter, a proximal end, a distal end in communication with the fluid, and a nanoparticle or nanobubble sensing zone between the proximal and the distal ends;
    (b) capturing a nanoparticle or nanobubble from the fluid into the nanopore;
    (c) translocating the captured nanoparticle or nanobubble across the sensing zone toward the proximal end by applying a differential pressure across the sensing zone, and/or by applying a voltage across the sensing zone, to provide a proximal translocation of the captured nanoparticle or nanobubble, and detecting a resistive pulse caused by the proximal translocation;
    (d) triggering, upon detection of the resistive pulse caused by the proximal translocation, a reversal of the direction of the differential pressure, and/or a reversal of the voltage across the sensing zone, and translocating the captured nanoparticle or nanobubble across the sensing zone toward the distal end to provide a distal translocation of the captured nanoparticle or nanobubble, and detecting a resistive pulse caused by the distal translocation;

(e) triggering, upon detection of the resistive pulse caused by the distal translocation, a reversal of the direction of the differential pressure, and/or a reversal of the voltage across the sensing zone, and translocating the captured nanoparticle or nanobubble across the sensing zone toward the proximal end to provide an additional proximal translocation of the captured nanoparticle or nanobubble;

(f) repeating (d) and (e) to provide for multiple proximal and distal translocations of the captured nanoparticle or nanobubble across the sensing zone and detecting multiple respective resistive pulses; and (g) determining a size and/or shape of the captured nanoparticle or nanobubble based on properties of the detected multiple resistive pulses.

2. The method of claim 1, wherein translocating in (c), (d), (e), and (f) is by applying a differential pressure across the sensing zone.

3. The method of claim 2, wherein applying the differential pressure across the sensing zone comprises use of a differential pressure regulator capable of controlling the pressure inside the nanopore relative to an external pressure, and wherein the pressure inside the nanopore can be positive or negative relative to the external pressure.

4. The method of claim 1, wherein translocating in (c), (d), (e), and (f) is by applying a voltage across the sensing zone using electrodes.

5. The method of claim 4, wherein applying a voltage across the sensing zone comprises use of electrodes positioned on opposite sides of the conical-shaped nanopore, the electrodes in communication with a voltage/potential source, and configured to provide for application of a voltage/potential across the sensing zone.

6. The method of claim 1, wherein the fluid is an aqueous saline solution.

7. The method of any claim 1, wherein the sensing zone of the conical-shaped nanopore has a half-cone angle sufficiently small to provide for significant channel-like character at the nanopore.

8. The method of claim 1, wherein determining in (g) comprises analyzing current-time traces of the multiple resistive pulses.

9. The method of claim 8, wherein analyzing the current-time traces of the multiple resistive pulses comprises exporting and analyzing the current time-traces using suitable computer-implemented data acquisition hardware and software.

10. The method of claim 9, wherein the computer-implemented data acquisition hardware and software comprises a data acquisition (DAQ) card.

11. The method of claim 9, wherein the computer-implemented data acquisition hardware and software comprises a field-programmable gate array (FPGA) card.

12. The method of claim 1, wherein the nanoparticles or nanobubbles have a diameter in a range selected from the size range group consisting of 8 nM to 10 nM, 8 nM to 20 nM, 8 nM to 30 nM, 8 nM to 40 nM, 8 nM to 50 nM, 8 nM to 100 nM and 100 nm to 1 micron.

13. The method of claim 1, wherein in f) the steps of d) and e) are repeated for a number of times selected from the group consisting of at least 2, at least 5, at least 10, at least 15, at least 20, at least 25, at least 30, at least 40, at least 50, at least 60, at least 70, at least 80, at least 90 and at least 100 times.

14. The method of claim 13, wherein in (f) the steps of (d) and (e) are repeated for a number of times selected from the group consisting of at least 40, at least 50 and at least 60 times.

15. The method of claim 1, wherein in (f) the steps of (d) and (e) repeated multiple times within a time period selected from the group consisting of 20 milliseconds, 40 milliseconds, 100 milliseconds, 0.5 second, 1 second, 5 seconds, 10 seconds, 30 seconds and 1 min.

16. The method of claim 1, wherein in (f) the steps of (d) and (e) are repeated multiple times, with each cycle (repeat frequency) being about 20 milliseconds.

17. The method of claim 16, wherein repeating in (f) of steps (d) and (e) is for multiple times within a time period of about of 30 seconds.

18. The method of claim 8, wherein determining in (g) comprises determining the radius of the nanoparticle or nanobubble.

19. The method of claim 8, wherein determining in (g) comprises determining the shape of the nanoparticle or nanobubble.

20. The method of claim 19 wherein the determined shape is spherical, asphericity, oblate, or prolate.

21. The method of claim 2, wherein the differential/applied pressure, in one direction or another (+ or −), is between 0.2 and 10 psi, between −5 psi and 5 psi, or between about −1 psi and 3 psi.

22. The method of claim 1, wherein the half-cone angle of the conical nanopore has a value in the range of 0.1 degrees to 4 degrees, to provide for achieving a suitable balance of the forces controlling dynamics of the nanoparticle or nanobubble.

23. The method of claim 22, wherein the half-cone angle of the conical nanopore has a value in the range of about 2 degrees.

24. The method of claim 22, wherein the half-cone angle of the conical nanopore has a value in the range of 0.2 degrees to 4 degrees.

25. The method of claim 22, wherein the half-cone angle of the conical nanopore has a value in the range of 0.3 degrees to 4 degrees, to provide for achieving the delicate balance of the forces controlling the particle dynamics.

26. The method of claim 22, wherein the half-cone angle of the conical nanopore has a value in the range of 0.4 degrees to 4 degrees.

27. The method of claim 1, wherein the nanoparticles or nanobubbles have a diameter of less than 8 nM, less than 10 nM, less than 20 nM, less than 30 nM, less than 40 nM, less than 50 nM, or less than 100 nm.

28. The method of claim 4, wherein the applied voltage/potential, in one direction or another (+ or −), is between 100 and 500 mV, −100 mV and 900 mV, between −250 mV and 900 mV, or about 250 mV.

29. The method of claim 6, wherein the salt concentration is between 100 mM and 1 M, 300 mM and 1 M, 500 mM and 1 M, about 150 mM, about 300 mM, or from 150 mM to about 300 mM sodium chloride.

30. The method of claim 1, wherein the size and/or shape of nanobubbles in solution is determined in solution, and wherein the nanobubbles are oxygen nanobubbles.

31. The method of claim 1, wherein the saline solution is RNS60 as known in the art.

32. The method of claim 29, wherein the salt concentration is between 100 and 300 mM, or about 150 mM.

33. A system or device for determining the size and/or shape of nanobubbles and nanoparticles in solution, comprising:
- a conduit, for a fluid having nanoparticles or nanobubbles, configured to be placed in communication with a source of the fluid;
- a conical-shaped nanopore (e.g., conical-shaped glass nanopore) having a half-cone angle, a nanopore diameter, a proximal end, a distal end in communication with the fluid conduit, the conical-shaped nanopore having a nanoparticle or nanobubble sensing zone between the proximal and the distal ends, and wherein the sensing zone of the conical-shaped nanopore has a half-cone angle sufficiently small to provide for significant channel-like character at the nanopore;
- a chamber containing the saline solution and the nanopore, wherein the chamber is in communication with a source of pressure;
- electrodes positioned on opposite sides of the conical-shaped nanopore, the electrodes in communication with a voltage/potential source, and configured to provide for application of a voltage/potential across the nanoparticle or nanobubble sensing zone between the proximal and the distal ends to provide an electrophoretic force (EPF) across the nanopore;
- a nanopore/electrode holder in communication with a differential pressure regulator capable of maintaining the pressure inside the conical-shaped nanopore at a constant pressure which can be positive or negative relative to the pressure of the chamber;
- a current measuring component configured to be in operative communication with computer-implemented data acquisition software suitable to analyze and export current-time traces; and
- control means for adjusting at least one parameter selected from voltage across and pressure inside the nanopore, to provide for fine control of particle or nanobubble translocation velocities across the sensing zone of the nanopore, to provide a method for detecting, manipulating and characterizing nanobubbles and nanoparticles in solution.

34. The system or device of claim 33, further comprising suitable computer-implemented data acquisition hardware and software for exporting and analyzing current-time traces of multiple resistive pulses.

35. The system of claim 34, comprising a data acquisition (DAQ) card and/or a field-programmable gate array (FPGA) card.

36. The system of claim 34, wherein the software is suitable to determine translocation peak parameters such as peak position, height, and width at half-height as a function of applied voltage.

37. The system of claim 33, wherein the current measuring component comprises a amplifier.

* * * * *

UNITED STATES PATENT AND TRADEMARK OFFICE
CERTIFICATE OF CORRECTION

PATENT NO. : 9,753,009 B2
APPLICATION NO. : 14/885935
DATED : September 5, 2017
INVENTOR(S) : German et al.

It is certified that error appears in the above-identified patent and that said Letters Patent is hereby corrected as shown below:

On the Title Page

In Column 1 (page 2, item (56)) at Line 15, Under Other Publications, change "Matericals" to --Materials--.

In Column 1 (page 2, item (56)) at Line 51, Under Other Publications, change "SUrface" to --Surface--.

In Column 2 (page 2, item (56)) at Line 36, Under Other Publications, change "ananofluidics," to --nanofluidics,--.

In Column 2 (page 2, item (56)) at Line 44, Under Other Publications, change "electoosmosis" to --electroosmosis--.

In Column 2 (page 2, item (56)) at Line 45, Under Other Publications, change "micofluidics" to --microfluidics--.

In Column 2 (page 2, item (56)) at Line 52, Under Other Publications, change "Goverend" to --Governed--.

In the Specification

In Column 7 at Line 26, Change "MO" to --M$\Omega$--.

In Column 7 at Line 54, Change "FIGS." to --FIG.--.

In Column 8 at Line 14, Change "Crosssectional" to --Cross-sectional--.

In Column 8 at Line 32, Change "resisitve" to --resistive--.

Signed and Sealed this
Thirty-first Day of July, 2018

Andrei Iancu
*Director of the United States Patent and Trademark Office*

CERTIFICATE OF CORRECTION (continued)
U.S. Pat. No. 9,753,009 B2

In Column 9 at Line 3, Change "mmHg" to --mmHg.--.

In Column 10 at Line 11, Change "resisitve" to --resistive--.

In Column 12 at Line 56, Change "hyprochorite)" to --hypochlorite)--.

In Column 14 at Line 46, Change "~70 nm" to --~70 nm.--.

In Column 18 at Line 56, Change "1.0°," to --1.0°),--.

In Column 24 at Line 33, Change "electroosmottic" to --electroosmotic--.

In Column 25 at Line 18, Change "J" to --J.--.

In Column 27 at Line 64, Change "nmnm" to --nm--.

In Column 32 at Line 53, Change "widthsat" to --widths at--.

In Column 37 at Line 41 (approx.), Change "J O/S ssang," to --Jo/ssang,--.

In Column 37 at Line 47 (approx.), Change "79" to --79.--.

In Column 37 at Line 48, Change "J O/S ssang," to --Jo/ssang,--.

In Column 38 at Line 20, Change "Particleswith" to --Particles with--.

In the Claims

In Column 39 at Line 42, In Claim 7, after "of" delete "any".